United States Patent
Kim et al.

(10) Patent No.: US 11,555,213 B2
(45) Date of Patent: Jan. 17, 2023

(54) NUCLEIC ACID ENCODING A MODIFIED HOMOSERINE DEHYDROGENASE

(71) Applicant: CJ CHEILJEDANG CORPORATION, Seoul (KR)

(72) Inventors: Hyo Jin Kim, Suwon-si (KR); Lan Huh, Suwon-si (KR); Sang Jo Lim, Incheon (KR); Hyun Ah Kim, Suwon-si (KR); Hyoung Joon Kim, Seoul (KR); Chang il Seo, Incheon (KR); Seung Bin Lee, Suwon-si (KR); Ji Sun Lee, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 17/472,028

(22) Filed: Sep. 10, 2021

(65) Prior Publication Data

US 2021/0403962 A1    Dec. 30, 2021

Related U.S. Application Data

(62) Division of application No. 16/483,309, filed as application No. PCT/KR2019/006083 on May 21, 2019, now Pat. No. 11,236,374.

(30) Foreign Application Priority Data

May 28, 2018  (KR) .......................... 10-2018-0060445

(51) Int. Cl.
| | |
|---|---|
| *C12N 9/04* | (2006.01) |
| *C12P 13/06* | (2006.01) |
| *C12N 1/20* | (2006.01) |
| *C12P 13/08* | (2006.01) |
| *C12P 13/12* | (2006.01) |

(52) U.S. Cl.
CPC ................ *C12P 13/06* (2013.01); *C12N 1/20* (2013.01); *C12N 9/0006* (2013.01); *C12P 13/08* (2013.01); *C12P 13/12* (2013.01); *C12Y 101/01003* (2013.01)

(58) Field of Classification Search
CPC ........... C12P 13/06; C12P 13/08; C12P 13/12; C12N 1/20; C12N 9/0006; C12N 15/52; C12N 15/77; C12Y 101/01003
See application file for complete search history.

(56) References Cited

U.S. PATENT DOCUMENTS

| | | | |
|---|---|---|---|
| 5,124,257 A | 6/1992 | Azizian et al. | |
| 6,649,379 B1 | 11/2003 | Archer et al. | |
| 7,332,310 B2 | 2/2008 | Nakagawa et al. | |
| 8,283,152 B2 | 10/2012 | Kim et al. | |
| 8,609,396 B2 | 12/2013 | Kim et al. | |
| 9,127,257 B2 | 9/2015 | Kim et al. | |
| 2009/0253186 A1 | 10/2009 | Kim et al. | |
| 2009/0298136 A1 | 12/2009 | Zelder et al. | |

FOREIGN PATENT DOCUMENTS

| | | |
|---|---|---|
| CN | 101208427 A | 6/2008 |
| KR | 10-0057684 B1 | 8/1992 |
| KR | 10-0159812 B1 | 11/1998 |
| KR | 10-2000-0041583 A | 7/2000 |
| KR | 10-0620092 B1 | 9/2006 |
| KR | 10-2008-0028940 A | 4/2008 |
| KR | 10-0924065 B1 | 10/2009 |
| KR | 10-1167853 B1 | 7/2012 |
| KR | 10-1429815 B1 | 8/2014 |
| KR | 10-1632642 B1 | 6/2016 |
| KR | 10-1783170 B1 | 9/2017 |
| WO | 2004/108894 A2 | 12/2004 |
| WO | 2007/086618 A1 | 8/2007 |
| WO | 2009/051262 A1 | 4/2009 |
| WO | 2010/084995 A2 | 7/2010 |

OTHER PUBLICATIONS

Archer et al., "A C-terminal deletion in *Corynebacterium glutamicum* homoserine dehydrogenase abolishes allosteric inhibition by L-threonine," *Gene* 107:53-59, 1991.
Branden et al., "Introduction to Protein Structure," Garland Publishing Inc., New York, p. 247 (1991).
Eikmanns et al., "Amplification of three threonine biosynthesis genes in *Corynebacterium glutamicum* and its influence on carbon flux in different strains," *Applied Microbiology and Biotechnology* 34:617-622, 1991.
GenBank Accession No. WP_012084404, May 16, 2013.
GenBank Accession No. WP_005816736, May 25, 2013.
Guo et al., "Protein tolerance to random amino acid change," *PNAS* 101(25):9205-9210 (Jun. 22, 2004).
"Homoserine dehydrogenase," *UniProtKB*, https://www.uniprot.org/uniprot/P08499, accessed: Jul. 8, 2019.
Morbach et al., "Engineering the homoserine dehydrogenase and threonine dehydratase control points to analyse flux towards L-isoleucine in *Corynebacterium glutamicum*," *Appl Microbiol Biotechnol* 45:612-620, 1996.
Morbach et al., "L-Isoleucine Production with *Corynebacterium glutamicum*: Further Flux Increase and Limitation of Export," *Applied and Environmental Microbiology* 62(12):4345-4351, 1996.
Peoples et al., "Nucleotide sequence and fine structural analysis of the *Corynebacterium glutamicum* hom-thrB operon," *Molecular Microbiology* 2(1):63-72, 1988. (11 pages).
Rey et al., "The putative transcriptional repressor McbR, member of the TetR-family, is involved in the regulation of the metabolic network directing the synthesis of sulfur containing amino acids in *Corynebacterium glutamicum*," *Journal of Biotechnology* 103:51-65, 2003.
Sadowski et al., "The sequence-structure relationship and protein function prediction," *Current Opinion in Structural Biology* 19:357-362 (2009).

(Continued)

*Primary Examiner* — Delia M Ramirez
(74) *Attorney, Agent, or Firm* — Seed IP Law Group LLP

(57) ABSTRACT

The present disclosure relates to modified homoserine dehydrogenase and a method for producing a homoserine-derived L-amino acid using the same.

2 Claims, No Drawings

Specification includes a Sequence Listing.

(56) References Cited

OTHER PUBLICATIONS

Seffernick et al., "Melamine Deaminase and Atrazine Chlorohydrolase: 98 Percent Identical but Functionally Different," *Journal of Bacteriology* 183(8):2405-2410 (2001).
Takeda et al., "Detection of K-ras Mutation in Sputum by Mutant-Allele-Specific Amplification (MASA)," *Human Mutation* 2:112-117, 1993.
Tang et al., "Identification of *Dehalobacter* reductive dehalogenases that catalyse dechlorination of chloroform, 1,1,1-trichloroethane and 1,1-dichloroethane," *Phil Trans R Soc B* 368:20123018, 1-10 (2013).
Van der Rest et al., "A heat shock following electroporation induces highly efficient transformation of *Corynebacterium glutamicum* with xenogeneic plasmid DNA," *Applied Microbiology and Biotechnology* 52:541-545, 1999.
Witowski et al., "Conversion of a β-Ketoacyl Synthase to a Malonyl Decarobxylase by Replacement of the Active-Site Cysteine with Glutamine," *Biochemistry* 38:11643-11650 (1999).

NUCLEIC ACID ENCODING A MODIFIED HOMOSERINE DEHYDROGENASE

CROSS REFERENCE TO RELATED APPLICATIONS

The present application is a divisional application of U.S. application Ser. No. 16/483,309 filed Aug. 2, 2019, now U.S. Pat. No. 11,236,374. which is a U.S. national phase application of PCT/KR2019/006083, filed May 21, 2019, which claims priority to KR Application No. 10-2018-0060445, filed May 28, 2018. U.S. application Ser. No. 16/483,309 is herein incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_450USPC_SEQUENCE_LISTING.txt. The text file is 53 KB, was created on Sep. 9, 2021, and is being submitted electronically via EFS-Web.

TECHNICAL FIELD

The present disclosure relates to modified homoserine dehydrogenase. Specifically, the present disclosure relates to modified homoserine dehydrogenase having a polypeptide comprising one or more amino acid substitutions in an amino acid sequence of a protein having the activity of homoserine dehydrogenase, wherein the amino acid substitution is carried out by substituting the amino acid at position 285 with isoleucine; the amino acid at position 398 with glutamine; or the amino acids at both positions with isoleucine and glutamine, respectively. In addition, the present disclosure relates to a method for producing homoserine or a homoserine-derived L-amino acid using the modified homoserine dehydrogenase, a composition for producing homoserine or a homoserine-derived L-amino acid, a method for increasing the ability to produce homoserine or a homoserine-derived L-amino acid, or a use of the modified homoserine dehydrogenase.

BACKGROUND ART

Among L-amino acids, L-threonine, L-isoleucine, and L-methionine commonly use homoserine produced by homoserine dehydrogenase (hereinafter referred to as "Hom"; EC:1.1.1.3) from aspartate-semialdehyde (hereinafter referred to as "ASA"). Therefore, in order to produce the amino acids via a fermentation method, it is essential to maintain the activities of enzymes used in the biosynthetic pathway at a certain level or higher, and intensive research thereon has been conducted.

In particular, the activity of homoserine dehydrogenase acting at the branch point of the biosynthetic pathways of L-lysine and L-threonine is known to be regulated by L-threonine and L-isoleucine. Recently, there have been several reports on Hom desensitized to feedback inhibition by L-threonine and a method for producing L-threonine using the same. In 1991, Eikmann et al. in Germany reported Hom desensitized by substituting glycine, which is the amino acid residue at position 378 of Hom, with glutamate (Eikmanns B J et al., Appl. Microbial Biotechnol. 34: 617-622, 1991); and in 1991, Archer et al. reported that desensitization occurs when the C-terminus of Hom is damaged due to a frame-shift mutation (Archer J A et al., Gene 107: 53-59, 1991).

DISCLOSURE

Technical Problem

The present inventors have conducted a study on desensitization to feedback inhibition by threonine, and as a result, they have found that a novel gene encoding modified Hom is isolated, and that the L-amino acid-producing ability is improved in a microorganism in which the novel gene is transduced, thereby completing the present disclosure.

Technical Solution

An object of the present disclosure is to provide modified homoserine dehydrogenase having a polypeptide comprising one or more amino acid substitutions in an amino acid sequence of a protein having the activity of homoserine dehydrogenase, wherein the amino acid substitution is carried out by substituting the amino acid at position 285 with another amino acid; the amino acid at position 398 with another amino acid; or the amino acids at both positions with other amino acids.

Another object of the present disclosure is to provide a polynucleotide encoding the modified dehydrogenase.

Still another object of the present disclosure is to provide a microorganism of the genus *Corynebacterium*, comprising the modified homoserine dehydrogenase.

Still another object of the present disclosure is to provide a method for producing homoserine or a homoserine-derived L-amino acid, comprising: culturing the microorganism in a medium; and recovering homoserine or a homoserine-derived L-amino acid from the microorganism or medium.

Still another object of the present disclosure is to provide a composition for producing homoserine or a homoserine-derived L-amino acid, which comprises the modified homoserine dehydrogenase or a microorganism comprising the modified homoserine dehydrogenase of the present disclosure.

Still another object of the present disclosure is to provide a method for increasing the ability to produce homoserine or a homoserine-derived L-amino acid, which comprises expressing the modified homoserine dehydrogenase of the present disclosure in a microorganism of the genus *Corynebacterium*.

Still another object of the present disclosure is to provide a use of the modified homoserine dehydrogenase for producing the homoserine or homoserine-derived L-amino acid of the present disclosure.

Still another object of the present disclosure is to provide a use of the polynucleotide for producing the homoserine or homoserine-derived L-amino acid of the present disclosure.

Still another object of the present disclosure is to provide a use of the microorganism of the genus *Corynebacterium* for producing the homoserine or homoserine-derived L-amino acid of the present disclosure.

Still another object of the present disclosure is to provide a use of the composition for producing the homoserine or homoserine-derived L-amino acid of the present disclosure.

Advantageous Effects

The modified homoserine dehydrogenase of the present disclosure can be widely used for the mass production of effective homoserine or a homoserine-derived L-amino acid, because feedback inhibition by a final product is desensitized compared to the natural or wild type.

BEST MODE FOR CARRYING OUT THE INVENTION

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the above objects, an aspect of the present disclosure provides modified homoserine dehydrogenase having a polypeptide comprising one or more amino acid substitutions in an amino acid sequence of a protein having the activity of homoserine dehydrogenase, wherein the amino acid substitution is carried out by substituting the amino acid at position 285 or the amino acid at position 398 with another amino acid, or by a combination thereof.

Specifically, the present disclosure provides a homoserine dehydrogenase variant having a polypeptide comprising one or more amino acid substitutions in an amino acid sequence of a protein having the activity of homoserine dehydrogenase, wherein the amino acid substitution is carried out by substituting the amino acid at position 285 with isoleucine; the amino acid at position 398 with glutamine; or the amino acids at both positions with isoleucine and glutamine, respectively. More specifically, the present disclosure provides modified homoserine dehydrogenase, wherein in the amino acid sequence of SEQ ID NO: 1, the amino acid at position 285 is substituted with isoleucine; the amino acid at position 398 is substituted with glutamine; or the amino acids at both positions are substituted with isoleucine and glutamine, respectively.

In the present disclosure, homoserine dehydrogenase (EC: 1.1.1.3) refers to an enzyme that catalyzes the synthesis of homoserine, a common intermediate for the biosynthesis of methionine, threonine, and isoleucine in plants and microorganisms. In the present disclosure, homoserine dehydrogenase may be included regardless of its origin as long as it has the above conversion activity, and an enzyme derived from any organism (plants, microorganisms, etc.) may be used as the homoserine dehydrogenase. Specifically, the homoserine dehydrogenase may be derived from a microorganism of the genus *Corynebacterium*, and more specifically may be derived from *Corynebacterium glutamicum*. For example, the homoserine dehydrogenase may be a protein including the amino acid sequence of SEQ ID NO: 1. The protein including the amino acid sequence of SEQ ID NO: 1 may be interchangeably used with the term "protein having the amino acid sequence of SEQ ID NO: 1" or "protein consisting of the amino acid sequence of SEQ ID NO: 1".

In the present disclosure, various methods well known in the art may be used for the method for obtaining homoserine dehydrogenase. Examples of such methods include gene synthesis techniques including optimization of codons so as to obtain proteins at high efficiency in a microorganism of the genus *Corynebacterium*, which is commonly used for the expression of proteins, and methods for screening useful enzyme resources using bioinformatics based on the metagenome of microorganisms, but the methods are not limited thereto.

In the present disclosure, the protein having the activity of homoserine dehydrogenase does not exclude a mutation that can occur due to a meaningless sequence addition upstream or downstream of the amino acid sequence of a protein having the activity of homoserine dehydrogenase, e.g., the amino acid sequence of SEQ ID NO: 1, or a naturally occurring mutation, or a silent mutation therein. In addition, the protein having the same or corresponding activity to the protein including the amino acid sequence of SEQ ID NO: 1 corresponds to the protein having the activity of the homoserine dehydrogenase of the present disclosure. As a specific example, the protein having the activity of the homoserine dehydrogenase of the present disclosure may be a protein consisting of the amino acid sequence of SEQ ID NO: 1 or an amino acid sequence having a homology thereto of at least 80%, 90%, 95%, or 97%.

Additionally, although described as "a protein or a polypeptide including the amino acid sequence of a particular SEQ ID NO" in the present disclosure, it is apparent that any protein having an amino acid sequence with deletion, modification, substitution, or addition in part of the sequence can also belong to the scope of the present disclosure as long as the protein has an amino acid sequence with any of the above homologies and exhibits an effect corresponding to the above protein. For example, in the present disclosure, the protein having the activity of homoserine dehydrogenase may be homoserine dehydrogenase derived from *Corynebacterium glutamicum*. More specifically, the protein having the activity of homoserine dehydrogenase may be the amino acid sequence (SEQ ID NO: 1) of homoserine dehydrogenase derived from *Corynebacterium glutamicum* ATCC13032, the amino acid sequence (SEQ ID NO: 49) of homoserine dehydrogenase derived from *Corynebacterium glutamicum* ATCC14067, or the amino acid sequence (SEQ ID NO: 50) of homoserine dehydrogenase derived from *Corynebacterium glutamicum* ATCC13869. Since the homoserine dehydrogenases having the above sequences show a homology of 80%, 90%, 95%, or 97% or more to each other, and since the homoserine dehydrogenases exhibit effects corresponding to those of homoserine dehydrogenase, it is apparent that they are included in the protein having the activity of the homoserine dehydrogenase of the present disclosure.

As used herein, the term "homology" refers to the percentage of identity between two polynucleotide or polypeptide moieties. The homology refers to a degree of matching with a given amino acid sequence or nucleotide sequence, and may be expressed as a percentage. In the present disclosure, a homology sequence having an activity which is identical or similar to the given amino acid sequence or nucleotide sequence is expressed as "% homology". The homology between sequences from one moiety to another may be determined by techniques known in the art. For example, the homology may be confirmed using standard software, i.e., BLAST 2.0, for calculating parameters such as score, identity, and similarity, or by comparing sequences via Southern hybridization experiments, and the appropriate hybridization conditions to be defined may be determined by a method known to those skilled in the art (e.g., J. Sambrook et al., Molecular Cloning, A Laboratory Manual, $2^{nd}$ Edition, Cold Spring Harbor Laboratory press, Cold Spring Harbor, N.Y., 1989; F. M. Ausubel et al., Current Protocols in Molecular Biology, John Wiley & Sons, Inc., New York).

As used herein, the term "modification", "modified", or "variant" refers to a culture or an individual that shows an inheritable or non-heritable alternation in one stabilized phenotype. Specifically, the term "variant" may be intended to mean a variant in which its activity is efficiently increased because one or more amino acids in the amino acid sequence corresponding to a protein having the activity of homoserine dehydrogenase are modified compared to the wild-type, a native or non-modified one, or a variant in which feedback inhibition by isoleucine, threonine, or a derivative thereof is released, or a variant in which the increase in activity and feedback inhibition are both released.

In the present disclosure, the term "modified homoserine dehydrogenase" may be used interchangeably with "homoserine dehydrogenase variant". On the other hand, such variant may be non-naturally occurring.

Specifically, the modified homoserine dehydrogenase of the present disclosure may be a modified protein having a polypeptide comprising one or more amino acid substitutions in the amino acid sequence of a protein having the activity of homoserine dehydrogenase, wherein the amino acid substitution is carried out by substituting the amino acid at position 285 with isoleucine, the amino acid at position 398 with glutamine, or a combination thereof. The amino acid sequence of the protein having the activity of homoserine dehydrogenase is as described above, and may be, for example, the amino acid sequence of SEQ ID NO: 1. In addition, the amino acid at position 285 may be one in which threonine is substituted with isoleucine, and the amino acid at position 398 may be one in which arginine is substituted with glutamine.

Additionally, the modified homoserine dehydrogenase of the present disclosure may be a modified protein having a polypeptide comprising one or more amino acid substitutions in the amino acid sequence of a protein having the activity of homoserine dehydrogenase, wherein the amino acid substitution is carried out by substituting the amino acid at position 378 with tryptophan. In addition, the modified homoserine dehydrogenase of the present disclosure may be a modified protein having a polypeptide comprising one or more amino acid substitutions in the amino acid sequence of a protein having the activity of homoserine dehydrogenase, wherein the amino acid substitution is carried out by substituting the amino acid at position 285 with isoleucine, the amino acid at position 398 with glutamine, or a combination thereof; in this modified homoserine dehydrogenase, the amino acid at position 378 may be further substituted with tryptophan. More specifically, the amino acid at position 378 may be one in which glycine is substituted with tryptophan.

Even more specifically, the modified homoserine dehydrogenase of the present disclosure is a modified protein having a polypeptide comprising one or more amino acid substitutions in the amino acid sequence of SEQ ID NO: 1, wherein the amino acid substitution is carried out by substituting the amino acid at position 285 with isoleucine, the amino acid at position 398 with glutamine, or a combination thereof. For example, the modified homoserine dehydrogenase of the present disclosure may be a protein including the amino acid sequence of SEQ ID NO: 10, 11, 12, or 13. In addition, a mutation that can occur due to a meaningless sequence addition upstream or downstream of the amino acid sequence, a naturally occurring mutation, or a silent mutation therein is not excluded. In addition, the protein having the same or corresponding activity to the modified homoserine dehydrogenase corresponds to the protein having the activity of the homoserine dehydrogenase of the present disclosure. As a specific example, the modified homoserine dehydrogenase of the present disclosure may be a protein consisting of the amino acid sequence of SEQ ID NO: 10, 11, 12, or 13, or a protein having a homology to the above amino acid sequence of at least 80%, 90%, 95%, or 97%. Additionally, although described as "a protein or a polypeptide having the amino acid sequence of a particular SEQ ID NO" in the present disclosure, it is apparent that any protein having an amino acid sequence with deletion, modification, substitution, or addition in part of the sequence can also belong to the scope of the present disclosure as long as the protein has an amino acid sequence with any of the above homologies and exhibits an effect corresponding to the above protein.

Additionally, the modified homoserine dehydrogenase of the present disclosure is modified homoserine dehydrogenase having a polypeptide comprising one or more amino acid substitutions in the amino acid sequence of a protein having the activity of homoserine dehydrogenase. It is apparent that any protein which includes modification in which the amino acid at position 285 or 398 is substituted with another amino acid, and which exhibits an effect corresponding to the homoserine dehydrogenase, belongs to the scope of the present disclosure.

Additionally, unlike the wild-type or native protein, or a non-modified protein having the activity of homoserine dehydrogenase, the modified homoserine dehydrogenase of the present disclosure may be one in which feedback inhibition by a final product, i.e., isoleucine, threonine, methionine, or homoserine, a derivative or analogue thereof is released or desensitized. As used herein, the term "feedback inhibition" means that a final product of metabolism prevents the earlier-stage reaction. Therefore, when the feedback inhibition of homoserine dehydrogenase is released or desensitized, the productivity of homoserine and that of a homoserine-derived L-amino acid can be improved compared to when the feedback inhibition is not released or desensitized.

The homoserine-derived L-amino acid refers to an L-amino acid which can be biosynthesized using L-homoserine as a precursor, and is not limited as long as it is a material that can be biosynthesized from L-homoserine. The homoserine-derived L-amino acid may include not only a homoserine-derived L-amino acid but also a derivative thereof. For example, the homoserine-derived L-amino acid may be L-threonine, L-isoleucine, O-acetyl homoserine, O-succinyl-L-homoserine, O-phospho-L-homoserine, L-methionine, and/or L-glycine, but is not limited thereto. More specifically, the homoserine-derived L-amino acid may be L-threonine, L-isoleucine, O-acetyl homoserine, O-succinyl-L-homoserine, and/or L-methionine, but is not limited thereto.

Another aspect of the present disclosure provides a polynucleotide encoding the modified homoserine dehydrogenase.

The homoserine dehydrogenase and variant are as described above.

As used herein, the term "polynucleotide" is a nucleotide polymer composed of nucleotide monomers covalently bonded in a chain, and examples thereof are DNA or RNA strands having a predetermined or longer length, and more specifically, it refers to a polynucleotide fragment encoding the modified homoserine dehydrogenase. The polynucleotide encoding the modified protein of the present disclosure can be included without limitation as long as it has a polynucleotide sequence encoding the modified protein having the activity of the homoserine dehydrogenase of the present disclosure.

In the present disclosure, the polynucleotide encoding the amino acid sequence of the homoserine dehydrogenase variant may be specifically derived from a microorganism of the genus *Corynebacterium*, and more specifically derived from *Corynebacterium glutamicum*, but is not limited thereto.

Additionally, in the polynucleotide encoding the protein, various modifications may be made in the coding region without changing an amino acid sequence of the protein, due to codon degeneracy or in consideration of the codons preferred in an organism in which the protein is to be expressed. Specifically, the polynucleotide may be a polynucleotide including a polynucleotide sequence encoding the protein or a polynucleotide sequence having a homology to the above polynucleotide sequence of at least 80%, 90%, 95%, or 97%. In addition, it is apparent that a polynucleotide sequence with deletion, modification, substitution, or addition in part of the sequence can also belong to the scope of the present disclosure as long as it is a polynucleotide sequence encoding the protein having the above homologies and exhibiting an effect substantially the same as or corresponding to the above protein. The polynucleotide encoding the protein having the activity of the homoserine dehydrogenase of the present disclosure may have a polynucleotide sequence encoding the amino acid sequence of SEQ ID NO: 1. For example, the polynucleotide may have the polynucleotide sequence of SEQ ID NO: 48, but is not limited thereto. In addition, the polynucleotide encoding the modified homoserine dehydrogenase of the present disclosure may have a polynucleotide sequence encoding the polypeptide comprising one or more amino acid substitutions in the amino acid sequence of SEQ ID NO: 1, and specifically may have a polynucleotide sequence encoding SEQ ID NO: 10, 11, 12, or 13. For example, the polynucleotide may have the polynucleotide sequence of SEQ ID NO: 6, 7, 8, or 9, but is not limited thereto.

Additionally, a probe that can be prepared from a known gene sequence, for example, any sequence which hybridizes with a sequence complementary to all or part of the polynucleotide sequence under stringent conditions to encode a protein having the activity of the homoserine dehydrogenase of the present disclosure, may be also included without limitation. The "stringent conditions" mean conditions under which specific hybridization between polynucleotides is allowed. Such conditions are specifically described in the literature (e.g., J. Sambrook et al., infra). The stringent conditions may include, for example, conditions under which genes having high homology, 80% or higher homology, specifically 90% or higher homology, more specifically 95% or higher homology, much more specifically 97% or higher homology, still much more specifically 99% or higher homology are hybridized with each other and genes having homology lower than the above homology are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS. Hybridization requires that two polynucleotides contain complementary sequences, although depending on the stringency of the hybridization, mismatches between bases are possible. The term "complementary" is used to describe the relationship between nucleotide bases that are hybridizable with each other. For example, with respect to DNA, adenosine is complementary to thymine and cytosine is complementary to guanine. Therefore, the present disclosure may also include an isolated nucleotide fragment complementary to the entire sequence as well as a nucleotide sequence substantially similar thereto. Specifically, the polynucleotide having homology may be detected using hybridization conditions including a hybridization step at a $T_m$ value of 55° C. under the above-described conditions. Further, the $T_m$ value may be 60° C., 63° C., or 65° C., but is not limited thereto, and may be appropriately controlled by those skilled in the art depending on the purpose thereof. The appropriate stringency for hybridizing polynucleotides depends on the length of the polynucleotides and the degree of complementation, and these variables well known in the art (see Sambrook et al., supra, 9.50-9.51, 11.7-11.8).

Still another aspect of the present disclosure provides a microorganism comprising the modified homoserine dehydrogenase. Specifically, the present disclosure provides a microorganism of the genus *Corynebacterium* producing homoserine or a homoserine-derived L-amino acid, comprising the modified homoserine dehydrogenase. In addition, the present disclosure provides a microorganism of the genus *Corynebacterium* producing L-alanine, comprising the modified homoserine dehydrogenase. However, the present disclosure is not limited thereto.

The homoserine dehydrogenase and variant are as described above.

Specifically, the microorganism comprising the modified homoserine dehydrogenase of the present disclosure refers to a microorganism which inherently has the ability to produce homoserine or a homoserine-derived L-amino acid, or a microorganism to which the ability to produce homoserine or a homoserine-derived L-amino acid is imparted to its parent strain lacking the ability to produce homoserine or a homoserine-derived L-amino acid. Specifically, the microorganism comprising the homoserine dehydrogenase may be a microorganism expressing modified homoserine dehydrogenase, wherein in the amino acid sequence of SEQ ID NO: 1, the amino acid at position 285 is substituted with isoleucine; the amino acid at position 398 is substituted with glutamine; or the amino acids at both positions are substituted with isoleucine and glutamine, respectively, but the microorganism is not limited thereto. The microorganism may be a cell or microorganism which includes a polynucleotide encoding the modified homoserine dehydrogenase or which is capable of expressing a modified polypeptide by transforming into a vector including a polynucleotide encoding modified homoserine dehydrogenase. For the objects of the present disclosure, the host cell or microorganism may be any microorganism capable of producing homoserine or a homoserine-derived L-amino acid, which includes the modified polypeptide.

The microorganism comprising the modified homoserine dehydrogenase of the present disclosure has the improved ability to produce homoserine, a homoserine-derived L-amino acid, or L-alanine compared to the wild-type or a microorganism including a protein having the activity of modified homoserine dehydrogenase. Therefore, homoserine, a homoserine-derived L-amino acid, or L-alanine can be obtained in high yield from this microorganism.

In the present disclosure, the type of microorganism including the modified homoserine dehydrogenase is not particularly limited, but may be *Enterobacter* sp., *Escherichia* sp., *Erwinia* sp., *Serratia* sp., *Pseudomonas* sp., *Providencia* sp., *Corynebacterium* sp., or *Brevibacterium* sp. More specifically, the microorganism may be a microorganism of the genus *Corynebacterium*.

In the present disclosure, the "microorganism of the genus *Corynebacterium*" may be specifically *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, etc., but is not limited thereto. More specifically, in the present disclosure, the microorganism of the genus *Corynebacterium* may be *Corynebacterium glutamicum*.

Meanwhile, the microorganism comprising the modified homoserine dehydrogenase may be a microorganism into which a vector including a polynucleotide encoding a homoserine dehydrogenase variant is introduced, but is not limited thereto.

As used herein, the term "vector" refers to a DNA construct including the nucleotide sequence of the polynucleotide encoding a target protein, in which the target protein is operably linked to a suitable control sequence so that it can be expressed in an appropriate host. The control sequence includes a promoter capable of initiating transcription, any operator sequence for the control of the transcription, a sequence encoding an appropriate mRNA ribosome-binding domain, and a sequence controlling the termination of transcription and translation. The vector, after being transformed with a suitable host cell, may be replicated or function irrespective of the host genome, or may be integrated into the host genome itself.

The vector used in the present disclosure is not particularly limited, as long as it is able to replicate in the host cell, and any vector known in the art may be used. Examples of conventional vectors may include a natural or recombinant plasmid, cosmid, virus, and bacteriophage. For instance, pWE15, M13, MBL3, MBL4, IXII, ASHII, APII, t10, t11, Charon4A, and Charon21A may be used as a phage vector or cosmid vector; and pBR type, pUC type, pBluescriptII type, pGEM type, pTZ type, pCL type, and pET type may be used as a plasmid vector. Specifically, pACYC177, pACYC184, pCL, pECCG117, pUC19, pBR322, pMW118, and pCC1BAC vector may be used, but the vector is not limited thereto.

A vector usable in the present disclosure is not particularly limited, and any known expression vector may be used. In addition, a polynucleotide encoding a target protein in the chromosome may be inserted through a vector for chromosomal insertion. The insertion of the polynucleotide into the chromosome may be performed by any method known in the art (e.g., homologous recombination), but the method is not limited thereto. The selection marker may be additionally included to confirm a successful gene insertion into the chromosome. A selection marker is for screening the cells which are transformed with the vector, in other words, for determining whether the target polynucleotide molecule is inserted. The markers that provide selectable phenotypes such as drug resistance, auxotrophy, resistance to cell toxic agents, or expression of surface proteins may be used. In an environment treated with a selective agent, only the cells expressing the selection marker can survive, or cells show a different phenotype, and thus the successfully transformed cells can be selected through this method.

As used herein, the term "transformation" refers to the introduction of a vector including a polynucleotide encoding a target protein into a host cell in such a way that the protein encoded by the polynucleotide is expressed in the host cell. As long as the transformed polynucleotide can be expressed in the host cell, it can be either integrated into or placed in the chromosome of the host cell, or it can exist extrachromosomally. Further, the polynucleotide includes DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. The expression cassette may include a promoter operably linked to the polynucleotide, transcription terminator, ribosome binding sites, or translation terminator. The expression cassette may be in the form of a self-replicable expression vector. In addition, the polynucleotide may be introduced into the host cell as-is and operably linked to sequences required for expression in the host cell, but is not limited thereto. The transformation method includes any method of introducing a polynucleotide into a cell, and may be carried out by selecting a suitable standard technique known in the art, depending on a host cell. Examples of the method include electroporation, calcium phosphate (Ca($H_2PO_4$)$_2$, CaHPO$_4$, or Ca$_3$(PO$_4$)$_2$) precipitation, calcium chloride (CaCl$_2$)) precipitation, microinjection, a polyethyleneglycol (PEG) technique, a DEAE-dextran technique, a cationic liposome technique, a lithium acetate-DMSO technique, etc., but are not limited thereto.

Additionally, the term "operable linkage" means that the polynucleotide sequence is functionally linked to a promoter sequence that initiates and mediates transcription of the polynucleotide encoding the target protein of the present disclosure. The operable linkage can be prepared using a gene recombinant technique known in the art, and site-specific DNA cleavage and linkage can be prepared using a known lyase and ligase, but these are not limited thereto.

The microorganism comprising the modified homoserine dehydrogenase may be one which has been transformed to include the modified homoserine dehydrogenase in a microorganism of the genus *Corynebacterium*. For example, the microorganism of the genus *Corynebacterium* may include a strain resistant to 2-amino-3-hydroxy-valerate (AHV); a strain producing L-threonine by substituting leucine, which is the amino acid at position 377 of aspartate kinase (LysC), with lysine in order to resolve the feedback inhibition of LysC, which is the first important enzyme acting in the biosynthetic pathway of threonine; a strain producing L-isoleucine by substituting the amino acid at position 323 of the ilvA gene, which encodes L-threonine dehydratase (the first enzyme acting in the biosynthetic pathway of isoleucine) in the strain producing L-threonine, with alanine (Appl. Enviro. Microbiol., December 1996, p. 4345-4351); a strain producing O-acetyl homoserine by inactivating O-acetylhomoserine (thiol)-lyase, which is involved in the degradation pathway of O-acetyl homoserine, and cystathionine gamma-synthase; or a strain producing methionine by inactivating transcriptional regulatory factors of methionine and cysteine, but is not limited thereto.

Still another aspect of the present disclosure provides a method for producing homoserine or a homoserine-derived L-amino acid, comprising: culturing the microorganism in a medium; and recovering homoserine or a homoserine-derived L-amino acid from the microorganism or medium.

As described above, the microorganism may be a microorganism of the genus *Corynebacterium*, comprising the homoserine dehydrogenase variant of the present disclosure, and more specifically may be *Corynebacterium glutamicum*. In addition, the microorganism of the genus *Corynebacterium* or *Corynebacterium glutamicum* may be a microorganism producing homoserine or a homoserine-derived L-amino acid. The homoserine-derived L-amino acid may include not only a homoserine-derived L-amino acid but also a derivative thereof. For example, the homoserine-derived L-amino acid may be L-threonine, L-isoleucine, O-acetyl homoserine, O-succinyl-L-homoserine, O-phospho-L-homoserine, L-methionine, and/or L-glycine, but is not limited thereto. More specifically, the homoserine-derived L-amino acid may be L-threonine, L-isoleucine, O-acetyl homoserine, O-succinyl-L-homoserine, and/or L-methionine, but is not limited thereto. In addition, the microorganism of the genus *Corynebacterium* or *Corynebacterium glutamicum* may be a microorganism producing L-alanine.

The homoserine or homoserine-derived L-amino acid may be a culture medium of homoserine or a homoserine-derived L-amino acid, which is produced by the microorganism described in the present disclosure, a supernatant of the culture, a processed product thereof, or purified form thereof. It is apparent to those skilled in the art that the homoserine or homoserine-derived L-amino acid includes not only its neutral form but also a salt thereof.

A method for producing the homoserine or homoserine-derived L-amino acid can be easily determined by those skilled in the art under optimized cultivation conditions and enzyme activity conditions known in the art.

In the above method, the cultivation of the microorganism may be performed in a batch process, continuous process, fed-batch process, etc. known in the art, but the culture process is not particularly limited thereto. In particular, with respect to the cultivation conditions, the pH of the culture may be adjusted to a suitable pH (e.g., pH 5 to pH 9, specifically pH 6 to pH 8, and most specifically with an appropriate basic compound (e.g., sodium hydroxide, potassium hydroxide, or ammonia) or acidic compound (e.g., phosphoric acid or sulfuric acid), and the aerobic condition of the culture may be maintained by introducing oxygen or an oxygen-containing gas mixture to the culture. The cultivation temperature may generally be in the range of 20° C. to 45° C., and specifically 25° C. to 40° C. for about 10 to 160 hours, but the cultivation conditions are not limited thereto. The threonine, isoleucine, or acetyl homoserine produced by the above cultivation may be secreted into the culture or may be retained in the cells.

Additionally, examples of the carbon sources to be used in the culture medium may include sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid), but are not limited thereto. These carbon sources may be used alone or in combination, but are not limited thereto. Examples of the nitrogen sources to be used in the culture medium may include nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. These nitrogen sources may be used alone or in combination, but are not limited thereto. Examples of the phosphorus sources to be used in the culture medium may include potassium dihydrogen phosphate, dipotassium hydrogen phosphate, corresponding sodium-containing salts, etc., but are not limited thereto. Additionally, metal salts (e.g., magnesium sulfate or iron sulfate), amino acids, vitamins, etc., which are essential growth-promoting materials, may be contained in the medium.

In the present disclosure, the method for recovering the homoserine or homoserine-derived L-amino acid produced in the step of cultivation may be performed by collecting the target product from the culture broth using an appropriate method known in the art. For example, methods such as centrifugation, filtration, anion exchange chromatography, crystallization, HPLC, etc. may be used, and the desired material, which is the homoserine or homoserine-derived L-amino acid, can be recovered from a culture or cultured microorganism using an appropriate method known in the art. Further, the recovery may include an additional purification process and may be performed using an appropriate method known in the art. An additional process may be inserted to increase the recovery of a target product before/after the cultivation step or the recovery step.

Still another aspect of the present disclosure provides a composition for producing homoserine or a homoserine-derived L-amino acid, which comprises the modified homoserine dehydrogenase or a microorganism comprising the modified homoserine dehydrogenase of the present disclosure.

The composition for producing homoserine or a homoserine-derived L-amino acid refers to a composition capable of producing homoserine or a homoserine-derived L-amino acid, in which the composition comprises modified homoserine dehydrogenase, wherein in the amino acid sequence of SEQ ID NO: 1, the amino acid at position 285 is substituted with isoleucine, the amino acid at position 398 is substituted with glutamine, or the amino acids at both positions are substituted with isoleucine and glutamine, respectively; a polynucleotide encoding the modified homoserine dehydrogenase; or a microorganism comprising the polynucleotide. For example, the polynucleotide may include an additional constitution capable of operating the polynucleotide without limitation. For example, the polynucleotide may be in a form included in a vector so that the operably linked gene can be expressed in the introduced host cell.

Additionally, the composition may further include any suitable excipient commonly used in compositions for producing homoserine or homoserine-derived L-amino acids. The excipient may be, for example, a preservative, a humectant, a dispersant, a suspending agent, a buffer, a stabilizer, an isotonic agent, etc., but is not limited thereto.

Still another aspect of the present disclosure provides a method for increasing the ability to produce homoserine or a homoserine-derived L-amino acid in a microorganism, which comprises substituting the amino acid at position 285 with isoleucine; the amino acid at position 398 with glutamine; or the amino acids at both positions with isoleucine and glutamine, respectively, in the amino acid sequence of SEQ ID NO: 1 having homoserine dehydrogenase activity.

The terms "homoserine dehydrogenase", and "homoserine or homoserine-derived L-amino acid" are as described above.

Still another aspect of the present disclosure provides a use of the modified homoserine dehydrogenase for producing homoserine or a homoserine-derived L-amino acid.

Still another aspect of the present disclosure provides a use of a polynucleotide encoding the modified homoserine dehydrogenase for producing homoserine or a homoserine-derived L-amino acid.

Still another aspect of the present disclosure provides a use of a microorganism of the genus *Corynebacterium*, which comprises the modified homoserine dehydrogenase, for producing homoserine or a homoserine-derived L-amino acid.

Still another aspect of the present disclosure provides a use of the composition for producing homoserine or a homoserine-derived L-amino acid, for producing homoserine or a homoserine-derived L-amino acid.

MODE FOR CARRYING OUT THE INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Screening for AHV-Resistant Microorganisms Through Artificial Modification In this Example, an experiment of imparting resistance against 2-amino-3-hydroxy-valerate (hereinafter referred to as "AHV"), which is an L-threonine analogue, was conducted using *Corynebacterium glutamicum* KFCC10881 (Korean Patent No. 0159812) as a parent strain, in order to release the feedback inhibition by L-threonine of homoserine dehydrogenase (hereinafter referred to as "Hom", EC:1.1.1.3).

Modification was induced by an artificial modification method using N-methyl-N'-nitro-N-nitrosoguanidine (hereinafter referred to as "NTG"). The KFCC10881 strain, which had been cultured in a seed medium for 18 hours, was inoculated into 4 mL of the seed medium, and then cultured until $OD_{660}$ reached about 1.0. The culture medium was centrifuged to recover the cells, and then the cells were washed twice with a 50 mM Tris-malate buffer (pH 6.5) and suspended in the final 4 mL of the same buffer. An NTG solution (2 mg/mL in a 0.05 M Tris-malate buffer (pH 6.5)) was added to the cell suspension to have a final concentration of 150 mg/L, and then allowed to stand at room temperature for 20 minutes. Thereafter, the cells were recovered by centrifugation, and washed twice with the same buffer to remove the NTG. The finally washed cells were suspended in 4 mL of a 20% glycerol solution and then stored at −70° C. until use. The NTG-treated strains were plated on a minimal medium containing 3 g/L of AHV, and then 155 AHV-resistant KFCC10881 strains were obtained through the above procedure.

Seed Medium (pH 7.0)

glucose 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100 µg, thiamine HCl 1,000 µg, calcium pantothenate 2,000 µg, nicotinamide 2,000 µg (based on 1 L of distilled water)

Minimal Medium (pH 7.2)

glucose 5 g, $KH_2PO_4$ 1 g, $(NH_4)_2SO_4$ 5 g, $MgSO_4.7H_2O$ 0.4 g, NaCl 0.5 g, biotin 200 µg, thiamine HCl 100 µg, calcium pantothenate 100 µg, nicotinamide 0.03 g, urea 2 g, $Na_2B_4O_7$ $10H_2O$ 0.09 mg, $(NH_4)_6Mo_7O_{27}$ $4H_2O$ 0.04 mg, $ZnSO_4$ $7H_2O$ 0.01 mg, $CuSO_4$ $5H_2O$, $MnCl_2$ $4H_2O$ 0.01 mg, $FeCl_3$ $6H_2O$ 1 mg, $CaCl_2$) 0.01 mg (based on 1 L of distilled water)

Example 2: L-Threonine Production Test for AHV-Resistant KFCC10881 Strains

A test for the L-threonine producing-ability was conducted on the 155 AHV-resistant strains obtained in Example 1. The 155 strains obtained in Example 1 were inoculated into a corner-baffled flask (250 mL) containing the seed medium (25 mL), and then cultured with shaking at 30° C. at 200 rpm for 20 hours. The seed culture medium (1 mL) was inoculated into a corner-baffled flask (250 mL) containing the below L-threonine production medium (24 mL), and then cultured with shaking at 30° C. at 200 rpm for 48 hours.

L-Threonine Production Medium (pH 7.2)

glucose 30 g, $KH_2PO_4$ 2 g, urea 3 g, $(NH_4)_2SO_4$ 40 g, peptone 2.5 g, CSL (Sigma) 5 g (10 mL), $MgSO_4$ $7H_2O$ 0.5 g, leucine 400 mg, $CaCO_3$ 20 g (based on 1 L of distilled water)

After the culture, the amounts of the various amino acids produced using HPLC were measured. The concentrations of the culture media of the amino acids for the 22 strains, which are shown to have an excellent L-threonine-producing ability among the 155 strains experimented on, were shown in Table 1. The candidates for the 22 strains confirmed through the above procedure were named as KFCC10881-1 to KFCC10881-22.

TABLE 1

Experiments on L-Threonine Production of Excellent AHV-resistant Strains

| | OD | Thr | Hse | Gly | Ala | Ile | Lys | Thr + Hse + Gly + Ile |
|---|---|---|---|---|---|---|---|---|
| KFCC10881 | 58.5 | 0.0 | 0.1 | 0.3 | 0.1 | 0.0 | 13.3 | 0.4 |
| KFCC10881-1 | 60.1 | 2.0 | 1.5 | 2.8 | 1.6 | 2.7 | 5.7 | 7.7 |
| KFCC10881-2 | 57.1 | 3.0 | 2.2 | 0.8 | 3.1 | 1.3 | 12.5 | 7.3 |
| KFCC10881-3 | 47.3 | 2.8 | 2.3 | 0.8 | 3.4 | 1.4 | 10.5 | 7.3 |
| KFCC10881-4 | 51.7 | 3.2 | 2.1 | 0.8 | 3.2 | 1.3 | 13.4 | 7.4 |
| KFCC10881-5 | 58.4 | 3.1 | 2.2 | 0.8 | 3.3 | 1.3 | 12.4 | 7.4 |
| KFCC10881-6 | 52.6 | 3.4 | 2.5 | 0.7 | 3.4 | 1.0 | 12.8 | 7.6 |
| KFCC10881-7 | 14.2 | 0.4 | 0.2 | 0.3 | 0.2 | 0.6 | 11.1 | 1.5 |
| KFCC10881-8 | 55.8 | 3.0 | 2.0 | 0.8 | 3.3 | 1.3 | 13.0 | 7.1 |
| KFCC10881-9 | 44.3 | 3.2 | 2.8 | 0.6 | 3.1 | 0.9 | 12.6 | 7.5 |
| KFCC10881-10 | 47.5 | 3.7 | 3.0 | 0.7 | 3.4 | 0.8 | 12.6 | 8.2 |
| KFCC10881-11 | 57.0 | 2.7 | 1.8 | 0.7 | 3.4 | 1.2 | 11.6 | 6.4 |
| KFCC10881-12 | 51.8 | 3.3 | 3.5 | 0.6 | 3.2 | 0.9 | 12.4 | 8.3 |
| KFCC10881-13 | 49.8 | 3.0 | 2.3 | 0.7 | 3.4 | 1.3 | 12.8 | 7.3 |
| KFCC10881-14 | 62.7 | 2.4 | 2.1 | 2.5 | 3.2 | 3.0 | 3.3 | 10.0 |
| KFCC10881-15 | 62.4 | 2.9 | 2.7 | 0.7 | 3.2 | 1.1 | 12.3 | 7.4 |
| KFCC10881-16 | 59.6 | 2.8 | 2.5 | 0.8 | 3.3 | 1.3 | 11.4 | 7.4 |
| KFCC10881-17 | 24.1 | 0.1 | 0.2 | 0.2 | 1.6 | 0.2 | 10.4 | 0.7 |
| KFCC10881-18 | 60.5 | 2.6 | 2.5 | 0.7 | 3.2 | 1.0 | 12.3 | 6.8 |
| KFCC10881-19 | 60.0 | 3.0 | 1.9 | 2.8 | 2.7 | 3.0 | 5.4 | 9.3 |
| KFCC10881-20 | 65.8 | 2.7 | 2.0 | 0.8 | 3.4 | 1.4 | 13.0 | 6.9 |
| KFCC10881-21 | 17.3 | 0.3 | 0.3 | 0.3 | 0.2 | 0.6 | 11.1 | 1.5 |
| KFCC10881-22 | 60.1 | 3.5 | 1.9 | 2.0 | 2.5 | 2.8 | 2.7 | 10.2 |

As shown in Table 1, the amounts of L-threonine, L-homoserine, L-glycine, L-alanine, and L-isoleucine, which are produced by the 22 types of strains having resistance to AHV, were increased compared to a control group, whereas the amount of L-lysine was decreased.

The biosynthetic pathways of L-threonine and L-lysine are separated from aspartate-semialdehyde (hereinafter referred to as "ASA") as a starting point. That is, the amount of L-lysine produced is decreased as the amount of L-threonine produced is increased. Accordingly, the amounts of homoserine (Hse), L-glycine (Gly), and L-isoleucine (Ile), which can be by-products in the L-threonine biosynthetic pathway, may be increased as the amount of L-threonine produced is increased, and thus the total amount thereof produced (Thr+Hse+Gly+Ile) was also confirmed.

Therefore, among the AHV-resistant strains above, the 4 types of strains (KFCC10881-1, KFCC10881-14, KFCC10881-19, and KFCC10881-22), which have the reduced amount of L-lysine produced, the increased amount of L-threonine produced, and the increased total amount of Thr+Hse+Gly+Ile produced, were selected as the most excellent AHV-resistant strains.

Example 3: Analysis of Nucleotide Sequences of Strains Having Excellent Ability to Produce Threonine Derived from KFCC10881

In order to analyze the nucleotide sequences of the L-threonine biosynthesis enzymes of the strains selected in Example 1 above, the following experiment was conducted. Based on the gene information provided by the Kyoto Encyclopedia of Genes and Genomes (KEGG), each of the nucleotide sequence of hom (SEQ ID NO: 1, NCgl1136), which encodes homoserine dehydrogenase of *Corynebacterium glutamicum* ATCC13032, and the nucleotide sequence of thrB (SEQ ID NO: 2, Gene No. NCgl1137), which encodes homoserine kinase, was obtained. hom and thrB are known to consist of an operon structure (Peoples et al., Mol. Biol. 2(1):63-72, 1988).

In order to obtain the DNA fragment containing the hom-thrB operon of the selected strains, PCR was carried out using the genomic DNA of the strains as a template and a combination of primers of SEQ ID NO: 3 and SEQ ID NO: 4. PfuUltra™ high-fidelity DNA polymerase (Stratagene) was used as a polymerase for the PCR reaction. PCR conditions were as follows: denaturation at 96° C. for 30 seconds; annealing at 52° C. for 30 seconds; and polymerization at 72° C. for 3 minutes, and a total of 30 cycles were repeated. As a result, it was possible to amplify a gene fragment (2778 bp; SEQ ID NO: 5), which includes the nucleotide sequence (300 bp) containing a promoter site upstream of the initiation codon of SEQ ID NO: 1 to include the 200 bp downstream of termination codon of SEQ ID NO: 2.

The nucleotide sequence was determined using the above prepared primer by an ABI PRISM 3730XL Analyzer (96 capillary type; Applied Biosystems). In the nucleotide sequence corresponding to hom among the hom-thrB operon in KFCC10881-1, cytosine, which is the nucleotide at position 854 of SEQ ID NO: 1, was mutated to thiamine, and thus the ACT codon encoding the threonine residue was mutated to the ATT codon encoding the isoleucine residue (hereinafter referred to as "T285I modification"; SEQ ID NO: 6). In addition, in the nucleotide sequence corresponding to the hom-thrB operon in KFCC10881-14, guanine, which is the nucleotide at position 1193 of SEQ ID NO: 1, was mutated to adenine, and thus the CGA codon encoding the arginine residue was mutated to the CAA codon encoding the glutamine residue (hereinafter referred to as "R398Q modification"; SEQ ID NO: 7). In addition, in the nucleotide sequence corresponding to the hom-thrB operon in KFCC10881-19, guanine, which is the nucleotide at position 1132 of SEQ ID NO: 1, was mutated to cytosine, and thus the GGG codon encoding the glycine residue was mutated to the TGG codon encoding the tryptophan residue (hereinafter referred to as "G378W modification"; SEQ ID NO: 8). In addition, in the nucleotide sequence corresponding to hom-thrB operon in KFCC10881-22, guanine, which is the nucleotide at position 1132 of SEQ ID NO: 1, was mutated to adenine, and guanine, which is the nucleotide at position 1134, was mutated to cytosine, and thus the GGG codon encoding the glycine residue was mutated to AGC codon encoding the serine residue (hereinafter referred to as "G378S modification"; SEQ ID NO: 9). Meanwhile, no modification was discovered in thrB, corresponding to SEQ ID NO: 2.

In view of the nucleotide sequence analyses above, it was possible to consequently confirm that the feedback inhibition by L-threonine was desensitized as in the Hom (SEQ ID NO: 10) expressed in KFCC10881-1, threonine, which is the amino acid residue at position 285, was mutated to isoleucine (T285I modification); in the Hom (SEQ ID NO: 11) expressed in KFCC10881-14, arginine, which is the amino acid residue at position 398, was mutated to glutamine (R398Q modification); in the Hom (SEQ ID NO: 12) expressed in KFCC10881-19, glycine, which is the amino acid residue at position 378, was mutated to tryptophan (G378W modification); and in the Hom (SEQ ID NO: 13) expressed in KFCC10881-22, glycine, which is the amino acid residue at position 378, was mutated to serine (G378S modification).

Example 4: Preparation of Novel Strains to which Homoserine Dehydrogenase is Introduced The primers of SEQ ID NO: 14 and SEQ ID NO: 15 were prepared in order to prepare strains in which the variants (T285I, R398Q, G378W, and G378S) identified in Example 2 were introduced to the wild-type strains.

In order to prepare strains to which each of the T285I, R398Q, G378W, and G378S hom modifications are introduced, PCR was carried out using the genomic DNA extracted from each of the KFCC10811-1, KFCC10811-14, KFCC10811-19, and KFCC10811-22 strains as a template and using primers of SEQ ID NO: 14 and SEQ ID NO: 15. PfuUltra™ high-fidelity DNA polymerase (Stratagene) was used as a polymerase for the PCR reaction. PCR conditions were as follows: denaturation at 95° C. for 30 seconds; annealing at 55° C. for 30 seconds; and polymerization at 72° C. for 2 minutes, and a total of 28 cycles was repeated. As a result, a gene fragment (1668 bp) including a promoter site (about 300 bp) of the hom gene (1338 bp) was obtained. The amplified product was purified using a PCR Purification kit (QUIAGEN), and then used as an insert DNA fragment for the preparation of a vector. Meanwhile, after treating with a restriction enzyme smaI, the ratio of the molar concentration (M) of the pDZ vector heat-treated at 65° C. for 20 minutes to the insert DNA fragment amplified by the PCR above was set to be 1:2, and then these were cloned using an Infusion Cloning Kit (TaKaRa) according to its manual. Thereafter, the vectors, i.e., pDZ-T285I, pDZ-R398Q, pDZ-G378W, and pDZ-G378S, for introducing the T285I, R398Q, G378W, and G378S modifications on the chromosome were prepared.

*Corynebacterium glutamicum* ATCC13032 was transformed with each of the prepared vectors by electroporation. After the secondary crossover, strains substituted with each of the modified nucleotides on the chromosome were obtained. By using a combination of the primers listed below and using a MASA (Mutant Allele Specific Amplification) PCR technique (Takeda et al., Hum. Mutation, 2, 112-117 (1993)), the appropriateness of the substitution was primarily determined by selecting amplified strains in the combination of the primers corresponding to each of the modified sequences (CTR-T285I: SEQ ID NO: 16 and SEQ ID NO: 17; CTR-R398Q: SEQ ID NO: 16 and SEQ ID NO: 18; CTR-G378W: SEQ ID NO: 16 and SEQ ID NO: 19; and CTR-G378S: SEQ ID NO: 16 and SEQ ID NO: 20). In addition, analyses of the hom sequences of the selected strains were conducted to secondarily confirm the appropriateness of the substitution by using SEQ ID NO: 16 and SEQ ID NO: 21 and by analyzing the modified sequences in the same manner as in Example 2. The strains substituted with each of the modified nucleotides were named as CTR-T285I, CTR-R398Q, CTR-G378W, and CTR-G378S, respectively.

Example 5: Measurement of Activity of Homoserine Dehydrogenase

The activity of the enzyme Hom was measured in the prepared strains. The wild-type strain ATCC13032 in a control group and CTR-T285I, CTR-R398Q, CTR-G378W, and CTR-G378S prepared in Example 4 were inoculated into 25 mL of the seed medium, and then cultured until reaching the late log phase. The cells were recovered by centrifugation, washed twice with a 0.1 M potassium phosphate buffer (pH 7.6), and finally suspended in 2 mL of the same buffer containing glycerol at a concentration of 30%. The cell suspension was physically disrupted by a conventional glass bead vortexing method for 10 minutes, and then the supernatant was recovered through two centrifugations (13,000 rpm, 4° C., 30 minutes) and used as a crude extract for measuring the activity of the enzyme Hom. For the measurement of the activity of Hom, a coenzyme solution (0.1 mL) was added to a reaction solution for measuring the enzyme activity (a potassium phosphate (pH 7.0) buffer, 25 mM NADPH, 5 mM aspartate semi-aldehyde), and then reacted at 30° C. The Hom activity U was defined as the number of NADPH μmol consumed per minute according to the presence of L-threonine (0 mM, 10 mM), and the results of the enzyme activity are shown in Table 2 below.

TABLE 2

Measurement of Hom Activity (U) and Desensitization by L-threonine

| | Enzyme activity (U) according to the amount of L-threonine added (mM) | |
| --- | --- | --- |
| Strain | 0 mM | 10 mM |
| ATCC13032 | 0.92 | 0.02 |
| CTR-T285I | 1.11 | 0.82 |
| CTR-R398Q | 1.31 | 1.12 |
| CTR-G378W | 1.39 | 1.21 |
| CTR-G378S | 1.38 | 1.22 |

As a result of the experiment, it was confirmed that in the Hom containing each of the T285I, R398Q, G378W, and G378S modifications, inhibition of the activity was reduced under the condition of containing 10 mM L-threonine, unlike the wild-type Hom, and thus desensitization to L-threonine occurred.

Example 6: Preparation and Evaluation of Microorganism Strain of the Genus Corynebacterium Having Productivity of L-Threonine Strains producing L-threonine were developed from the wild-type Corynebacterium glutamicum ATCC13032. Specifically, in order to resolve the feedback inhibition of aspartate kinase (LysC), which is an important enzyme first acted upon in the threonine biosynthesis pathway, leucine, which is an amino acid at position 377 of LysC, was substituted with lysine (SEQ ID NO: 22).

More specifically, in order to prepare the strains in which the LysC (L377K) modification is introduced, PCR was carried out using the chromosome of ATCC13032 as a template and using primers of SEQ ID NOs: 23 and 24 or SEQ ID NOs: 25 and 26. PfuUltra™ high-fidelity DNA polymerase (Stratagene) was used as a polymerase for the PCR reaction. PCR conditions were as follows: denaturation at 95° C. for 30 seconds; annealing at 55° C. for 30 seconds; and polymerization at 72° C. for 1 minute, and a total of 28 cycles were repeated. As a result, a DNA fragment (515 bp) in the 5' upstream region and a DNA fragment (538 bp) in the 3' downstream region were each obtained with the modification site of the lysC gene as the center. PCR was carried out with the two amplified DNA fragments as a template using primers of SEQ ID NO: 23 and SEQ ID NO: 26. After denaturation at 95° C. for 5 minutes, PCR was carried out for a total of 28 cycles under the following conditions: denaturation at 95° C. for 30 seconds; annealing at 55° C. for 30 seconds; and polymerization at 72° C. for 2 minutes. Thereafter, the polymerization reaction was carried out at 72° C. for 5 minutes. As a result, the DNA fragment (1023 bp) including the modification of the lysC gene, which encodes an aspartokinase variant in which leucine at position 377 is substituted with lysine, was amplified. The amplified product was purified using a PCR Purification kit (QUIAGEN) and used as an insert DNA fragment for the preparation of a vector. Meanwhile, after treating with a restriction enzyme SmaI, the ratio of the molar concentration (M) of the pDZ vector heat-treated at 65° C. for 20 minutes to the insert DNA fragment amplified by the PCR above was set to be 1:2, and then these were cloned using an Infusion Cloning Kit (TaKaRa) according to its manual. Thereafter, the vector pDZ-L377K for introducing the L377K modification on the chromosome was prepared.

ATCC13032 was transformed with the prepared vector by electroporation. After the secondary crossover, a strain in which each of the nucleotide modifications is substituted with modified nucleotides was obtained, and the strain was named as CJP1.

In order to clearly confirm the L-threonine production change of the strain, each of the modifications identified in Example 4 was introduced into a gene encoding homoserine dehydrogenase. Specifically, in order to introduce each of the T285I, R398Q, G378W, and G378S modifications to the CTR-L377K strain, CJP1 was transformed with each of the pDZ-T285I, pDZ-R398Q, pDZ-G378W, and pDZ-G378S vectors prepared in Example 4 by electroporation, and then strains in which each of the nucleotide modifications is substituted with modified nucleotides on the chromosome were obtained by the secondary crossover as in the same manner as in Example 4. The strains substituted with each of the modified nucleotides were named as CJP1-T285I, CJP1-R398Q, CJP1-G378W, and CJP1-G378S.

The strains CJP1-T285I and CJP1-R398Q were deposited at the Korean Culture Center of Microorganisms (KCCM), which is an International Depository Authority under the Budapest Treaty, on Sep. 26, 2017, with Accession Nos. KCCM12119P and KCCM12120P, respectively.

TABLE 3

Confirmation of L-threonine-producing Ability of 4 Prepared Strains

| | Amino acid (g/L) | |
| --- | --- | --- |
| Strain | Thr | Lys |
| CJP1 | 0.40 | 3.60 |
| CJP1-T285I | 1.10 | 3.00 |
| CJP1-R398Q | 1.21 | 2.75 |
| CJP1-G378W | 1.30 | 2.68 |
| CJP1-G378S | 1.25 | 2.78 |

As a result, in the stains in which each of the modifications is introduced, the amount of L-lysine produced was decreased and the amount of L-threonine produced was increased by 0.7 g/L to 0.9 g/L, as compared with the CJP1 strain.

Meanwhile, in order to obtain a strain simultaneously including the T285I and R398Q modifications, the CJP1-T285I strain was transformed with the pDZ-R398Q vector, and then the strain (CJP1-T285I, R398Q) was obtained in by the same method as described above. In addition, in order to obtain a strain simultaneously including the G378W and R398Q modifications, the CJP1-G378W strain was transformed with the pDZ-R398Q vector, and then the strain (CJP1-G378W, R398Q) was obtained by the same method as described above. In addition, in order to obtain strains simultaneously including the T285I and G378W modifications, the CJP1-T285I strain was transformed with the pDZ-G378W vector, and then the strain (CJP1-T285I, G378W) was obtained by the same method as described above. The test on the ability to produce L-threonine was conducted by the method described in Example 2, and the results thereof are shown in Table 4 below.

TABLE 4

Confirmation of L-threonine-producing Ability of 3 Prepared Strains

| Strain | Amino acid (g/L) | |
|---|---|---|
| | Thr | Lys |
| CJP1 | 0.41 | 3.55 |
| CJP1-G378W | 1.30 | 2.68 |
| CJP1-T285I, R398Q | 1.41 | 2.65 |
| CJP1-G378W, R398Q | 2.12 | 1.92 |
| CJP1-T285I, G378W | 1.92 | 2.15 |

As a result, the threonine-producing ability was confirmed to be higher when the two types of modifications of the present disclosure were introduced, compared with the CJP1-G378W strain showing the highest threonine-producing ability in the Examples. In the strains in which the two modifications are introduced, the amount of threonine produced was increased by 1.1 g/L to 1.7 g/L compared to the CJP1 strain, which is a control group, and therefore, it was confirmed that the desensitization effect of Hom was greatly improved.

Example 7: Preparation and Evaluation of Microorganism Strain of the Genus *Corynebacterium* Producing L-Isoleucine In order to produce strains producing isoleucine, a vector was prepared for enhancing the expression of the modified ilvA (V323A) gene (Appl. Enviro. Microbiol., December 1996, p. 4345-4351), which encodes known L-threonine dehydratase (the first enzyme in the isoleucine biosynthesis pathway) in the strains prepared in Example 6.

Specifically, in order to prepare a vector for introducing a modification, which targets the ilvA gene, a pair of primers (SEQ ID NOs: 27 and 28) for amplifying the 5' upstream region and a pair of primers (SEQ ID NOs: 29 and 30) for amplifying the 3' downstream region were devised with the modification site as the center. BamHI restriction enzyme sites (underlined) were inserted at each terminus of the primers of SEQ ID NOs: 27 and 30, and the primers of SEQ ID NOs: 28 and 29 were designed such that a nucleotide-substituted modification (underlined) is positioned at a region where a cross-over is to be induced.

TABLE 5

| SEQ ID NO: | Nucleotide sequence |
|---|---|
| 27 | ACGGATCCCAGACTCCAAAGCAAAAGCG |
| 28 | ACACCACGgCAGAACCAGGTGCAAAGGACA |

TABLE 5-continued

| SEQ ID NO: | Nucleotide sequence |
|---|---|
| 29 | CTGGTTCTGcCGTGGTGTGCATCATCTCTG |
| 30 | ACGGATCCAACCAAACTTGCTCACACTC |

PCR was carried out with the chromosome of the wild-type as a template using primers of SEQ ID NOs: 27, 28, 29, and 30. After denaturation at 95° C. for 5 minutes, PCR was carried out for a total of 30 cycles under the following conditions: denaturation at 95° C. for 30 seconds; annealing at 55° C. for 30 seconds; and polymerization at 72° C. for 30 seconds. Thereafter, the polymerization reaction was carried out at 72° C. for 7 minutes. As a result, a DNA fragment (627 bp) in the 5' upstream region and a DNA fragment (608 bp) in the 3' downstream region were obtained with the modification site of the ilvA gene as the center.

PCR was carried out with the two amplified DNA fragments as a template using primers of SEQ ID NOs: 27 and 30. After denaturation at 95° C. for 5 minutes, PCR was carried out for a total of 30 cycles under the following conditions: denaturation at 95° C. for 30 seconds; annealing at 55° C. for 30 seconds, and polymerization at 72° C. for 60 seconds. Thereafter, the polymerization reaction was carried out at 72° C. for 7 minutes. As a result, the DNA fragment (1217 bp) was amplified, including the modification of the ilvA gene encoding the IlvA variant in which valine at position 323 is substituted with alanine. The vector pECCG117 (Korean Patent No. 10-0057684) and the DNA fragment (1011 bp) were treated with a restriction enzyme BamHI, ligated using DNA ligase, and then cloned to obtain a plasmid. The thus-obtained plasmid was named as pECCG117-ilvA (V323A).

The pECCG117-ilvA (V323A) vector was introduced to each of the CJP1-T285I,R398Q, CJP1-G378W,R398Q, and CJP1-T285I,G378W strains prepared in Example 6 by electroporation and smeared on a selective medium containing kanamycin (25 mg/L) to obtain transformed strains. The thus-obtained transformed strains were cultured by the same flask cultivation method of Example 2, and the concentrations of L-isoleucine in the culture media were analyzed. The results thereof are shown in Table 6.

TABLE 6

Evaluation of Prepared Strains

| Strain | L-Isoleucine (g/L) |
|---|---|
| CJP1/pECCG117-ilvA(V323A) | 0.7 |
| CJP1-G378W/pECCG117-ilvA(V323A) | 0.9 |
| CJP1-T285I, R398Q/pECCG117-ilvA(V323A) | 1.1 |
| CJP1-G378W, R398Q/pECCG117-ilvA(V323A) | 1.2 |
| CJP1-T285I, G378W/pECCG117-ilvA(V323A) | 1.0 |

As a result, it was confirmed that in the strain including the hom(G378W) modification, concentration of L-isoleucine was improved by 0.2 g/L compared to the control strain. In addition, in the strain including the hom modification, in which two modifications had been simultaneously introduced, the ability to produce L-isoleucine was further improved by 0.3 g/L to 0.5 g/L compared to the control strain. Further, among the prepared strains, 1.1 g/L of L-isoleucine was produced in the CJP1-T285I,R398Q/pECCG117-ilvA (V323A) strain including both T285I and R398Q modifications.

Example 8: Preparation and Evaluation of O-Acetyl-Homoserine (OAH)-Producing Strain Substituted with Modified Hom 8-1. Preparation of ATCC13032 Strain Substituted with Modified Hom The two types of modifications (T285I and R398Q) were introduced into the ATCC13032 strain in the same manner as in Example 7, and the thus-prepared strain was named as ATCC13032::Hom$^{FBR}$.

8-2. Deletion of metB Gene

In this example, the metB gene encoding cystathionine gamma-synthase in the O-acetyl-homoserine degradation pathway was obtained through PCR using the chromosomal DNA of *Corynebacterium glutamicum* ATCC13032 as a template. Based on GenBank of the National Institutes of Health (NIH GenBank), the information of the nucleotide sequence of the metB was obtained (NCBI Registration No. Ncgl2360; SEQ ID NO: 31). In addition, based on this, the primers (SEQ ID NOS: 32 and 33) containing the N-terminus and linker sequence of the metB gene and the primers (SEQ ID NOS: 34 and 35) containing the C-terminus and linker sequence of the metB gene were synthesized. PCR was carried out with the chromosomal DNA of *Corynebacterium glutamicum* ATCC13032 as a template using the oligonucleotides of the nucleotide sequences of SEQ ID NOS: 32 and 33 and SEQ ID NOS: 34 and 35 as the primers. PfuUltra™ high-fidelity DNA polymerase (Stratagene) was used as a polymerase. PCR conditions were as follows: denaturation at 96° C. for 30 seconds; annealing at 53° C. for 30 seconds; and polymerization at 72° C. for 1 minute, and a total of 30 cycles were repeated. As a result, an amplified gene (500 bp) containing the N-terminus and linker of the metB gene and an amplified gene (500 bp) containing the C-terminus and linker of the metB gene were obtained.

PCR was carried out using the two thus-obtained amplified genes as a template for a total of 10 cycles under the following conditions: denaturation at 96° C. for 60 seconds; annealing at 50° C. for 60 seconds; and polymerization at 72° C. for 1 minute. Thereafter, the nucleotide sequences of SEQ ID NOS: 32 and 35 were added thereto, and then a total of 20 cycles were repeated. As a result, an amplified ΔmetB gene (1000 bp), which is a metB inactivation cassette containing the N-terminal-linker-C-terminal of the metB gene, was obtained. The metB gene obtained though the PCR was treated with restriction enzymes XbaI and SalI included at the termini, and then cloned into a pDZ(KR 0924065) vector, in which the restriction enzymes XbaI and SalI are treated, via ligation. Thereafter, a recombinant pDZ-ΔmetB vector in which the metB inactivation cassette is finally cloned was prepared.

The *Corynebacterium glutamicum* ATCC13032 and ATCC13032::Hom$^{FBR}$ were transformed with the thus-prepared pDZ-metB vector. After secondary crossover, *Corynebacterium glutamicum* ATCC13032 ΔmetB and ATCC13032::Hom$^{FBR}$ ΔmetB, in which the metB gene is inactivated on the chromosome, were obtained. The inactivated metB gene was finally confirmed by carrying out PCR using primers of SEQ ID NOS: 32 and 25, and then it was compared with ATCC13032 in which the metB gene is not inactivated.

8-3. Deletion of metY Gene

In this Example, the metY gene encoding O-acetylhomoserine (thiol)-lyase in the O-acetyl-homoserine degradation pathway was obtained through PCR using the chromosomal DNA of *Corynebacterium glutamicum* ATCC13032 as a template. Based on GenBank of the National Institutes of Health (NIH GenBank), the information of the nucleotide sequence of the metY gene was obtained (NCBI Registration No. Ncgl0625; SEQ ID NO: 36). In addition, based on this, the primers (SEQ ID NOS: 37 and 38) containing the N-terminus and linker sequence of the metY gene and the primers (SEQ ID NOS: 39 and 40) containing the C-terminus and linker sequence of the metY gene were synthesized.

PCR was carried out with the chromosomal DNA of *Corynebacterium glutamicum* ATCC13032 as a template using the oligonucleotides of the nucleotide sequences of SEQ ID NOS: 39 and 40 as the primers. PfuUltra™ high-fidelity DNA polymerase (Stratagene) was used as a polymerase. PCR conditions were as follows: denaturation at 96° C. for 30 seconds; annealing at 53° C. for 30 seconds; and polymerization at 72° C. for 1 minute, and a total of 30 cycles were repeated. As a result, an amplified gene (500 bp) containing the N-terminus and linker of the metY gene and an amplified gene (500 bp) containing the C-terminus and linker of the metY gene were obtained. PCR was carried out using the two thus-obtained amplified genes as a template for a total of 10 cycles under the following conditions: denaturation at 96° C. for 60 seconds; annealing at 50° C. for 60 seconds; and polymerization at 72° C. for 1 minute. Thereafter, the nucleotide sequences of SEQ ID NOS: 37 and 40 were added thereto, and then a total of 20 cycles were repeated. As a result, an amplified ΔmetY gene (1000 bp), which is a metB inactivation cassette containing the N-terminal-linker-C-terminal of the metY gene, was obtained.

The metY gene obtained through the PCR was treated with restriction enzymes XbaI and SalI included at the termini, and then cloned into a pDZ(KR2008-0025355) vector, in which the restriction enzymes XbaI and SalI are treated, via ligation. Thereafter, a recombinant pDZ-ΔmetY vector in which the metY inactivation cassette is finally cloned was prepared.

The *Corynebacterium glutamicum* ATCC13032, ATCC13032::Hom$^{FBR}$, ATCC13032 ΔmetB, and ATCC13032::Hom$^{FBR}$ ΔmetB strains were transformed with the thus-prepared pDZ-ΔmetY vector. After secondary crossover, *Corynebacterium glutamicum* ATCC13032 ΔmetY, ATCC13032::Hom$^{FBR}$ ΔmetY, ATCC13032 ΔmetB ΔmetY, and ATCC13032::Hom$^{FBR}$ ΔmetB ΔmetY, in which the metY gene is inactivated on the chromosome, were obtained. The inactivated metY gene was finally confirmed by carrying out PCR using primers of SEQ ID NOS: 37 and 40, and then it was compared with ATCC13032 in which the metY gene is not inactivated.

8-4. Preparation and Evaluation of Strain Producing O-Acetyl-Homoserine

Comparison was made between the O-acetyl-homoserine-producing abilities of the ATCC13032, ATCC13032 ΔmetB, ATCC13032 ΔmetY, ATCC13032 ΔmetB ΔmetY, ATCC13032::Hom$^{FBR}$, ATCC13032::Hom$^{FBR}$ ΔmetB, ATCC13032::Hom$^{FBR}$ ΔmetY, and ATCC13032::Hom$^{FBR}$ ΔmetB ΔmetY strains prepared in Examples 8-1 to 8-3, in which the metB, metY, metBY gene are deleted and the modified hom gene is substituted.

Specifically, single colonies were cultured in an LB solid medium overnight in a 32° C. incubator, and one loopful of each of the single colonies was inoculated on O-acetyl-homoserine titer media (25 mL), and then the resultants were cultured at 32° C. at 250 rpm for 42 to 64 hours. The O-acetyl-homoserine from each of the cultured products was analyzed by HPLC, and the results thereof are shown in Table 7 below.

L-O-Acetylhomoserine Production Medium (pH 7.2)
glucose 30 g, $KH_2PO_4$ 2 g, urea 3 g, $(NH_4)_2SO_4$ 40 g, peptone 2.5 g, CSL (Sigma) 5 g (10 mL), $MgSO_4.7H_2O$ 0.5 g, methionine 400 mg, leucine 400 mg, $CaCO_3$ 20 g (based on 1 L of distilled water)

TABLE 7

Evaluation of O-Acetyl-Homoserine Production

| Strains | | O-AH production (g/L) |
|---|---|---|
| ATCC13032 | — | 0.0 |
| | metB | 0.3 |
| | metY | 0.3 |
| | metBY | 0.5 |
| ATCC13032::Hom$^{FBR}$ (T285I + R398Q) | — | 0.0 |
| | metB | 1.2 |
| | metY | 1.4 |
| | metBY | 3.5 |

As a result, as shown in Table 7 above, O-acetyl homoserine was not accumulated when *Corynebacterium glutamicum* ATCC13032, a control strain, was cultured; whereas each of 0.3 g/L, 0.3 g/L, and 0.5 g/L of O-acetyl homoserine was accumulated in the ATCC13032 ΔmetB, ATCC13032 ΔmetY, and ATCC13032 ΔmetB ΔmetY strains, respectively, in which the metB, metY, and metBY genes are inactivated.

Additionally, in the case of the ATCC13032::Hom$^{F1}$ strain in which the hom gene is substituted in a mutant form, and the ATCC13032::Hom$^{FBR}$ ΔmetB, ATCC13032::Hom$^{FBR}$ ΔmetY, and ATCC13032::Hom$^{FBR}$ ΔmetB ΔmetY strains in which the metB, metY, and metBY genes are inactivated, respectively, it was confirmed that O-acetyl homoserine was accumulated in an amount of 1.2 g/L, 1.4 g/L, and 3.5 g/L for each of these strains.

Therefore, from the results above, it was confirmed that the production amount of the target amino acid, which utilizes homoserine as a precursor by using the modified hom of the present disclosure, could be greatly increased.

Example 9: Preparation and Evaluation of Strain Producing Methionine (Met)

Example 9-1: Preparation of Recombinant Vector for Deletion of mcbR Gene

In this Example, in order to prepare strains producing methionine, a vector for inactivation of the mcbR gene (J. Biotechnol. 103:51-65, 2003), which encodes known methionine and cysteine transcription regulatory proteins in the strains prepared in Example 6, was prepared.

Specifically, a recombinant plasmid vector was prepared using the method below in order to knock out the mcbR gene on the chromosome of *Corynebacterium* ATCC13032. Based on nucleotide sequences reported in Genbank of the National Institutes of Health (NIH GenBank), the mcbR gene and its surrounding sequence (SEQ ID NO: 41) of *Corynebacterium glutamicum* were obtained.

For the purpose of obtaining the mcbR-deleted gene, PCR was carried out with the chromosomal DNA of *Corynebacterium glutamicum* ATCC13032 as a template using primers of SEQ ID NOS: 42 and 43 and SEQ ID NOS: 44 and 45. After denaturation at 95° C. for 5 minutes, PCR was carried out for a total of 30 cycles under the following conditions: denaturation at 95° C. for 30 seconds; annealing at 53° C. for 30 seconds; and polymerization at 72° C. for 30 seconds. As a result, DNA fragments (700 bp) were obtained.

A pDZ vector (Korean Patent No. 10-0924065), which cannot be cloned in *Corynebacterium glutamicum*, and the amplified mcbR gene fragments were treated with a restriction enzyme smaI for chromosomal introduction. Thereafter, they were ligated using DNA ligase, and then transformed with *E. coli* DH5a, followed by smearing the same on an LB solid medium containing kanamycin (25 mg/L). Colonies transformed with the vector, in which deleted fragments of the target genes are inserted through PCR, were selected, and a plasmid was obtained using a plasmid extraction method. The thus-obtained plasmid was named as pDZ-ΔmcbR.

Example 9-2: Preparation and Evaluation of Microorganism Strain of Genus *Corynebacterium* Producing L-Methionine Each of the CJP1-G378W, CJP1-T285I,R398Q, CJP1-G378W,R398Q, CJP1-T285I,G378W, and CJP1 strains, which had been prepared in Example 6 by homologous recombination on the chromosome, was transformed with the pDZ-ΔmcbR vector prepared in Example 9 using electroporation (van der Rest et al., Appl. Microbiol. Biotechnol. 52:541-545, 1999). Thereafter, secondary recombination was carried out on a solid medium containing X-gal. Strains in which the mcbR gene is deleted were confirmed by a PCR method with the transformed *Corynebacterium glutamicum* strains, in which the secondary recombination had been completed, using primers of SEQ ID NOS: 46 and 47. These recombinant strains were named as *Corynebacterium glutamicum* CJP1-G378W/ΔmcbR, CJP1-T285I,R398Q/ΔmcbR, CJP1-G378W,R398Q/ΔmcbR, CJP1-T285I,G378W/ΔmcbR, and CJP1/ΔmcbR, respectively.

In order to analyze the L-methionine-producing ability of the prepared CJP1-G378W/ΔmcbR, CJP1-T285I,R398Q/ΔmcbR, CJP1-G378W,R398Q/ΔmcbR, and CJP1-T285I,G378W/ΔmcbR strains, the strains were cultured together with their parent strain, *Corynebacterium glutamicum* CJP1/ΔmcbR, in the following manner.

*Corynebacterium glutamicum* CJP1/ΔmcbR and the inventive strains (*Corynebacterium glutamicum* CJP1-G378W/ΔmcbR, CJP1-T285I,R398Q/ΔmcbR, CJP1-G378W,R398Q/ΔmcbR, and CJP1-T285I,G378W/ΔmcbR) were inoculated into a corner-baffled flask (250 mL) containing the seed medium below (25 mL), and then cultured with shaking at 30° C. at 200 rpm for 20 hours. Thereafter, the seed culture medium (1 mL) was inoculated into a corner-baffled flask (250 mL) containing the production medium below (24 mL), and then cultured with shaking at 30° C. at 200 rpm for 48 hours. The compositions of the seed medium and production medium are as follows.

<Seed Medium (pH 7.0)>
glucose 20 g, peptone 10 g, yeast extract 5 g, urea 1.5 g, $KH_2PO_4$ 4 g, $K_2HPO_4$ 8 g, $MgSO_4.7H_2O$ 0.5 g, biotin 100 μg, thiamine HCl 1,000 μg, calcium pantothenate 2,000 μg, nicotinamide 2,000 μg (based on 1 L of distilled water)

<Production Medium (pH 8.0)>
glucose 50 g, $(NH_4)_2S_2O_3$ 12 g, yeast extract 5 g, $KH_2PO_4$ 1 g, $MgSO_4.7H_2O$ 1.2 g, biotin 100 μg, thiamine HCl 1,000 μg, calcium pantothenate 2,000 μs, nicotinamide 3000 μs, $CaCO_3$ 30 g (based on 1 L of distilled water)

After cultivation using the cultivation method above, the concentration of L-methionine in each culture medium was analyzed, and the results are shown in Table 8.

TABLE 8

Evaluation of Prepared Strains

| Strain | L-Methionine (g/L) |
| --- | --- |
| CJP1/ΔmcbR | 0.01 |
| CJP1-G378W/ΔmcbR | 0.13 |
| CJP1-T285I, R398Q/ΔmcbR | 0.18 |
| CJP1-G378W, R398Q/ΔmcbR | 0.20 |
| CJP1-T285I, G378W/ΔmcbR | 0.17 |

As a result, it was confirmed that in the strain including the G378W hom modification, the L-methionine-producing ability was improved by 0.12 g/L compared to the control strain. Additionally, it was confirmed that in the strains including the hom modification, in which two modifications had been simultaneously introduced, the L-methionine-producing ability was improved by 0.16 g/L to 0.19 g/L compared to the control strain.

Based on the results above, it was confirmed that the amount of L-methionine produced could be greatly increased by using the modified hom of the present disclosure.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

[Accession Number]

Name of Depositary Agency: Korean Culture Center of Microorganisms (International Depositary Authority)

Deposition Number: KCCM12119P

Date of Deposition: Sep. 26, 2017

Name of Depositary Agency: Korean Culture Center of Microorganisms (International Depositary Authority)

Deposition Number: KCCM12120P

Date of Deposition: Sep. 26, 2017

The invention claimed is:

1. A polynucleotide encoding a modified homoserine dehydrogenase having at least 95% sequence identity with the polypeptide of SEQ ID NO: 1, wherein said modified homoserine dehydrogenase comprises an isoleucine at the position corresponding to position 285 of the polypeptide of SEQ ID NO: 1, and/or a glutamine at the position corresponding to position 398 of the polypeptide of SEQ ID NO: 1, and wherein the modified homoserine dehydrogenase has homoserine dehydrogenase activity.

2. The polynucleotide according to claim 1, wherein said modified homoserine dehydrogenase further comprises a tryptophan at the position corresponding to position 378 of the polypeptide of SEQ ID NO: 1.

* * * * *

SEQUENCE LISTING

```
<160> NUMBER OF SEQ ID NOS: 50

<210> SEQ ID NO 1
<211> LENGTH: 445
<212> TYPE: PRT
<213> ORGANISM: Artificial Sequence
<220> FEATURE:
<223> OTHER INFORMATION: homoserine dehydrogenase

<400> SEQUENCE: 1

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
```

```
            180                 185                 190
Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
        210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
                260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
        290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Arg Ala Pro Gly Glu Ser Thr Tyr
                340                 345                 350

Ala Asn Leu Pro Ile Ala Asp Phe Gly Glu Thr Thr Thr Arg Tyr His
                355                 360                 365

Leu Asp Met Asp Val Glu Asp Arg Val Gly Val Leu Ala Glu Leu Ala
        370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
        420                 425                 430

Val Lys Ala Ile Asn Ser Val Ile Arg Leu Glu Arg Asp
        435                 440                 445

<210> SEQ ID NO 2
<211> LENGTH: 930
<212> TYPE: DNA
<213> ORGANISM: Artificial Sequence
<220> FEATURE:
<223> OTHER INFORMATION: thrB gene

<400> SEQUENCE: 2
atggcaattg aactgaacgt cggtcgtaag gttaccgtca cggtacctgg atcttctgca        60
aacctcggac ctggctttga cactttaggt ttggcactgt cggtatacga cactgtcgaa       120
gtggaaatta ttccatctgg cttggaagtg gaagtttttg cgaaggcca aggcgaagtc        180 cctcttgatg gctcccacct ggtggttaaa gctattcgtg ctggcctgaa ggcagctgac       240
gctgaagttc tggattgcg agtggtgtgc cacaacaaca ttccgcagtc tcgtggtctt        300
ggctcctctg ctgcagcggc ggttgctggt gttgctgcag ctaatggttt ggcggatttc       360
ccgctgactc aagagcagat tgttcagttg tcctctgcct ttgaaggcca cccagataat       420
gctgcggctt ctgtgctggg tgagcagtg gtgtcgtgga caaatctgtc tatcgacggc       480
aagagccagc acagtatgc tgctgtacca cttgaggtgc aggacaatat tcgtgcgact       540
gcgctggttc ctaatttcca cgcatccacc gaagctgtgc gccgagtcct tcccactgaa       600
```

```
gtcactcaca tcgatgcgcg atttaacgtg tcccgcgttg cagtgatgat cgttgcgttg    660
cagcagcgtc ctgatttgct gtgggagggt actcgtgacc gtctgcacca gccttatcgt    720
gcagaagtgt tgcctattac ctctgagtgg gtaaaccgcc tgcgcaaccg tggctacgcg    780 gcatacctttccggtgccgg cccaaccgcc atggtgctgt ccactgagcc aattccagac    840
aaggttttgg aagatgctcg tgagtctggc attaaggtgc ttgagcttga ggttgcggga    900
ccagtcaagg ttgaagttaa ccaaccttag                                     930

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
ctgcgacagc atggaact                                                   18

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
caacgacaaa cgcccatc                                                   18

<210> SEQ ID NO 5
<211> LENGTH: 2778
<212> TYPE: DNA
<213> ORGANISM: Artificial Sequence
<220> FEATURE:
<223> OTHER INFORMATION: gene fragment

<400> SEQUENCE: 5
ctgcgacagc atggaactca gtgcaatggc tgtaaggcct gcaccaacaa tgattgagcg     60
aagctccaaa atgtcctccc cgggttgata ttagatttca taaatatact aaaaatcttg    120
agagtttttc cgttgaaaac taaaaagctg ggaaggtgaa tcgaatttcg gggctttaaa    180
gcaaaaatga acagcttggt ctatagtggc taggtaccct ttttgttttg gacacatgta    240
gggtggccga aacaaagtaa taggacaaca acgctcgacc gcgattattt ttggagaatc    300
atgacctcag catctgcccc aagctttaac cccggcaagg gtcccggctc agcagtcgga    360
attgcccttt taggattcgg aacagtcggc actgaggtga tgcgtctgat gaccgagtac    420
ggtgatgaac ttgcgcaccg cattggtggc ccactggagg ttcgtggcat tgctgtttct    480
gatatctcaa agccacgtga aggcgttgca cctgagctgc tcactgagga cgcttttgca    540
ctcatcgagc gcgaggatgt tgacatcgtc gttgaggtta tcggcggcat tgagtaccca    600
cgtgaggtag ttctcgcagc tctgaaggcc ggcaagtctg ttgttaccgc caataaggct    660
cttgttgcag ctcactctgc tgagcttgct gatgcagcgg aagccgcaaa cgttgacctg    720
tacttcgagg ctgctgttgc aggcgcaatt ccagtggttg ccccactgcg tcgctccctg    780
gctggcgatc agatccagtc tgtgatgggc atcgttaacg gcaccaccaa cttcatcttg    840
gacgccatgg attccaccgg cgctgactat gcagattctt tggctgaggc aactcgtttg    900
ggttacgccg aagctgatcc aactgcagac gtcgaaggcc atgacgccgc atccaaggct    960
```

| | |
|---|---|
| gcaattttgg catccatcgc tttccacacc cgtgttaccg cggatgatgt gtactgcgaa | 1020 |
| ggtatcagca acatcagcgc tgccgacatt gaggcagcac agcaggcagg ccacaccatc | 1080 |
| aagttgttgg ccatctgtga aagttcacc aacaaggaag gaaagtcggc tatttctgct | 1140 |
| cgcgtgcacc cgactctatt acctgtgtcc cacccactgg cgtcggtaaa caagtccttt | 1200 |
| aatgcaatct tgttgaagc agaagcagct ggtcgcctga tgttctacgg aaacggtgca | 1260 |
| ggtggcgcgc caaccgcgtc tgctgtgctt ggcgacgtcg ttggtgccgc acgaaacaag | 1320 |
| gtgcacggtg gccgtgctcc aggtgagtcc acctacgcta acctgccgat cgctgatttc | 1380 |
| ggtgagacca ccactcgtta ccacctcgac atggatgtgg aagatcgcgt gggggttttg | 1440 |
| gctgaattgg ctagcctgtt ctctgagcaa ggaatctccc tgcgtacaat ccgacaggaa | 1500 |
| gagcgcgatg atgatgcacg tctgatcgtg gtcacccact ctgcgctgga atctgatctt | 1560 |
| tcccgcaccg ttgaactgct gaaggctaag cctgttgtta aggcaatcaa cagtgtgatc | 1620 |
| cgcctcgaaa gggactaatt ttactgacat ggcaattgaa ctgaacgtcg gtcgtaaggt | 1680 |
| taccgtcacg gtacctggat cttctgcaaa cctcggacct ggctttgaca ctttaggttt | 1740 |
| ggcactgtcg gtatacgaca ctgtcgaagt ggaaattatt ccatctggct tggaagtgga | 1800 |
| agttttggc gaaggccaag gcgaagtccc tcttgatggc tcccacctgg tggttaaagc | 1860 |
| tattcgtgct ggcctgaagg cagctgacgc tgaagttcct ggattgcgag tggtgtgcca | 1920 |
| caacaacatt ccgcagtctc gtggtcttgg ctcctctgct gcagcggcgg ttgctggtgt | 1980 |
| tgctgcagct aatggtttgg cggatttccc gctgactcaa gagcagattg ttcagttgtc | 2040 |
| ctctgccttt gaaggccacc agataatgc tgcggcttct gtgctgggtg gagcagtggt | 2100 |
| gtcgtggaca atctgtctca tcgacggcaa gagccagcca cagtatgctg ctgtaccact | 2160 |
| tgaggtgcag gacaatattc gtgcgactgc gctggttcct aatttccacg catccaccga | 2220 |
| agctgtgcgc cgagtccttc ccactgaagt cactcacatc gatgcgcgat ttaacgtgtc | 2280 |
| ccgcgttgca gtgatgatcg ttgcgttgca gcagcgtcct gatttgctgt gggagggtac | 2340 |
| tcgtgaccgt ctgcaccagc cttatcgtgc agaagtgttg cctattacct ctgagtgggt | 2400 |
| aaaccgcctg cgcaaccgtg gctacgcggc ataccttttcc ggtgccggcc caaccgccat | 2460 |
| ggtgctgtcc actgagccaa ttccagacaa ggttttggaa gatgctcgtg agtctggcat | 2520 |
| taaggtgctt gagcttgagg ttgcgggacc agtcaaggtt gaagttaacc aaccttaggc | 2580 |
| ccaacaagga aggccccctt cgaatcaaga aggggccctt attagtgcag caattattcg | 2640 |
| ctgaacacgt gaaccttaca ggtgcccggc gcgttgagtg gtttgagttc cagctggatg | 2700 |
| cggttgtttt caccgaggct ttcttggatg aatccggcgt ggatggcgca gacgaaggct | 2760 |
| gatgggcgtt tgtcgttg | 2778 |

<210> SEQ ID NO 6
<211> LENGTH: 1338
<212> TYPE: DNA
<213> ORGANISM: Artificial Sequence
<220> FEATURE:
<223> OTHER INFORMATION: T285I

<400> SEQUENCE: 6

| | |
|---|---|
| atgacctcag catctgcccc aagctttaac cccggcaagg gtcccggctc agcagtcgga | 60 |
| attgcccttt taggattcgg aacagtcggc actgaggtga tgcgtctgat gaccgagtac | 120 |
| ggtgatgaac ttgcgcaccg cattggtggc ccactggagg ttcgtggcat tgctgtttct | 180 |
| gatatctcaa agccacgtga aggcgttgca cctgagctgc tcactgagga cgcttttgca | 240 |

```
ctcatcgagc gcgaggatgt tgacatcgtc gttgaggtta tcggcggcat tgagtaccca    300
cgtgaggtag ttctcgcagc tctgaaggcc ggcaagtctg ttgttaccgc caataaggct    360
cttgttgcag ctcactctgc tgagcttgct gatgcagcgg aagccgcaaa cgttgacctg    420
tacttcgagg ctgctgttgc aggcgcaatt ccagtggttg ccccactgcg tcgctccctg    480
gctggcgatc agatccagtc tgtgatgggc atcgttaacg gcaccaccaa cttcatcttg    540
gacgccatgg attccaccgg cgctgactat gcagattctt tggctgaggc aactcgtttg    600
ggttacgccg aagctgatcc aactgcagac gtcgaaggcc atgacgccgc atccaaggct    660
gcaattttgg catccatcgc tttccacacc cgtgttaccg cggatgatgt gtactgcgaa    720
ggtatcagca acatcagcgc tgccgacatt gaggcagcac agcaggcagg ccacaccatc    780
aagttgttgg ccatctgtga aagttcacc aacaaggaag aaagtcggc tatttctgct    840 cgcgtgcacc cgattctatt acctgtgtcc cacccactgg cgtcggtaaa caagtccttt    900
aatgcaatct tgttgaagc agaagcagct ggtcgcctga tgttctacgg aaacggtgca    960
ggtggcgcgc caaccgcgtc tgctgtgctt ggcgacgtcg ttggtgccgc acgaaacaag   1020
gtgcacggtg ccgtgctcc aggtgagtcc acctacgcta acctgccgat cgctgatttc   1080
ggtgagacca ccactcgtta ccacctcgac atggatgtgg aagatcgcgt ggggttttg   1140 gctgaattgg ctagcctgtt ctctgagcaa ggaatctccc tgcgtacaat ccgacaggaa   1200
gagcgcgatg atgatgcacg tctgatcgtg gtcacccact ctgcgctgga atctgatctt   1260
tcccgcaccg ttgaactgct gaaggctaag cctgttgtta aggcaatcaa cagtgtgatc   1320
cgcctcgaaa gggactaa                                                 1338
```

<210> SEQ ID NO 7  
<211> LENGTH: 1338  
<212> TYPE: DNA  
<213> ORGANISM: Artificial Sequence  
<220> FEATURE:  
<223> OTHER INFORMATION: R398Q

<400> SEQUENCE: 7

```
atgacctcag catctgcccc aagctttaac cccggcaagg gtcccggctc agcagtcgga     60
attgcccttt taggattcgg aacagtcggc actgaggtga tgcgtctgat gaccgagtac    120
ggtgatgaac ttgcgcaccg cattggtggc ccactggagg ttcgtggcat tgctgtttct    180
gatatctcaa agccacgtga aggcgttgca cctgagctgc tcactgagga cgcttttgca    240
ctcatcgagc gcgaggatgt tgacatcgtc gttgaggtta tcggcggcat tgagtaccca    300
cgtgaggtag ttctcgcagc tctgaaggcc ggcaagtctg ttgttaccgc caataaggct    360
cttgttgcag ctcactctgc tgagcttgct gatgcagcgg aagccgcaaa cgttgacctg    420
tacttcgagg ctgctgttgc aggcgcaatt ccagtggttg ccccactgcg tcgctccctg    480
gctggcgatc agatccagtc tgtgatgggc atcgttaacg gcaccaccaa cttcatcttg    540
gacgccatgg attccaccgg cgctgactat gcagattctt tggctgaggc aactcgtttg    600
ggttacgccg aagctgatcc aactgcagac gtcgaaggcc atgacgccgc atccaaggct    660
gcaattttgg catccatcgc tttccacacc cgtgttaccg cggatgatgt gtactgcgaa    720
ggtatcagca acatcagcgc tgccgacatt gaggcagcac agcaggcagg ccacaccatc    780
aagttgttgg ccatctgtga aagttcacc aacaaggaag aaagtcggc tatttctgct    840 cgcgtgcacc cgactctatt acctgtgtcc cacccactgg cgtcggtaaa caagtccttt    900
```

```
aatgcaatct tgttgaagc agaagcagct ggtcgcctga tgttctacgg aaacggtgca      960
ggtggcgcgc caaccgcgtc tgctgtgctt ggcgacgtcg ttggtgccgc acgaaacaag    1020
gtgcacggtg gccgtgctcc aggtgagtcc acctacgcta acctgccgat cgctgatttc    1080
ggtgagacca ccactcgtta ccacctcgac atggatgtgg aagatcgcgt gggggttttg    1140
gctgaattgg ctagcctgtt ctctgagcaa ggaatctccc tgcgtacaat ccaacaggaa    1200
gagcgcgatg atgatgcacg tctgatcgtg gtcacccact ctgcgctgga atctgatctt    1260
tcccgcaccg ttgaactgct gaaggctaag cctgttgtta aggcaatcaa cagtgtgatc    1320
cgcctcgaaa gggactaa                                                  1338

<210> SEQ ID NO 8
<211> LENGTH: 1338
<212> TYPE: DNA
<213> ORGANISM: Artificial Sequence
<220> FEATURE:
<223> OTHER INFORMATION: G378W

<400> SEQUENCE: 8
atgacctcag catctgcccc aagctttaac cccggcaagg gtcccggctc agcagtcgga      60
attgcccttt taggattcgg aacagtcggc actgaggtga tgcgtctgat gaccgagtac    120
ggtgatgaac ttgcgcaccg cattggtggc ccactggagg ttcgtggcat tgctgttttct    180 gatatctcaa agccacgtga aggcgttgca cctgagctgc tcactgagga cgcttttgca    240
ctcatcgagc gcgaggatgt tgacatcgtc gttgaggtta tcggcggcat tgagtaccca    300
cgtgaggtag ttctcgcagc tctgaaggcc ggcaagtctg ttgttaccgc caataaggct    360
cttgttgcag ctcactctgc tgagcttgct gatgcagcgg aagccgcaaa cgttgacctg    420
tacttcgagg ctgctgttgc aggcgcaatt ccagtggttg gcccactgcg tcgctccctg    480
gctggcgatc agatccagtc tgtgatgggc atcgttaacg gcaccaccaa cttcatcttg    540
gacgccatga ttccaccggc gctgactat gcagattctt tggctgaggc aactcgtttg    600
ggttacgccg aagctgatcc aactgcagac gtcgaaggcc atgacgccgc atccaaggct    660
gcaattttgg catccatcgc tttccacacc cgtgttaccg cggatgatgt gtactgcgaa    720
ggtatcagca acatcagcgc tgccgacatt gaggcagcac agcaggcagg ccacaccatc    780
aagttgttgg ccatctgtga aagttcacc aacaaggaag aaagtcggc tatttctgct    840 cgcgtgcacc cgactctatt acctgtgtcc cacccactgg cgtcggtaaa caagtccttt    900
aatgcaatct tgttgaagc agaagcagct ggtcgcctga tgttctacgg aaacggtgca    960
ggtggcgcgc caaccgcgtc tgctgtgctt ggcgacgtcg ttggtgccgc acgaaacaag   1020
gtgcacggtg gccgtgctcc aggtgagtcc acctacgcta acctgccgat cgctgatttc   1080
ggtgagacca ccactcgtta ccacctcgac atggatgtgg aagatcgcgt gtgggttttg   1140
gctgaattgg ctagcctgtt ctctgagcaa ggaatctccc tgcgtacaat ccgacaggaa   1200
gagcgcgatg atgatgcacg tctgatcgtg gtcacccact ctgcgctgga atctgatctt   1260
tcccgcaccg ttgaactgct gaaggctaag cctgttgtta aggcaatcaa cagtgtgatc   1320
cgcctcgaaa gggactaa                                                 1338

<210> SEQ ID NO 9
<211> LENGTH: 1338
<212> TYPE: DNA
<213> ORGANISM: Artificial Sequence
<220> FEATURE:
<223> OTHER INFORMATION: G378S
```

<400> SEQUENCE: 9

```
atgacctcag catctgcccc aagctttaac cccggcaagg gtcccggctc agcagtcgga      60
attgcccttt taggattcgg aacagtcggc actgaggtga tgcgtctgat gaccgagtac     120
ggtgatgaac ttgcgcaccg cattggtggc ccactggagg ttcgtggcat tgctgtttct     180
gatatctcaa agccacgtga aggcgttgca cctgagctgc tcactgagga cgcttttgca     240
ctcatcgagc gcgaggatgt tgacatcgtc gttgaggtta tcggcggcat tgagtaccca     300
cgtgaggtag ttctcgcagc tctgaaggcc ggcaagtctg ttgttaccgc caataaggct     360
cttgttgcag ctcactctgc tgagcttgct gatgcagcgg aagccgcaaa cgttgacctg     420
tacttcgagg ctgctgttgc aggcgcaatt ccagtggttg gcccactgcg tcgctccctg     480
gctggcgatc agatccagtc tgtgatgggc atcgttaacg gcaccaccaa cttcatcttg     540
gacgccatgg attccaccgg cgctgactat gcagattctt ggctgaggc aactcgtttg     600
ggttacgccg aagctgatcc aactgcagac gtcgaaggcc atgacgccgc atccaaggct     660
gcaattttgg catccatcgc tttccacacc cgtgttaccg cggatgatgt gtactgcgaa     720
ggtatcagca acatcagcgc tgccgacatt gaggcagcac agcaggcagg ccacaccatc     780
aagttgttgg ccatctgtga aagttcacc aacaaggaag aaagtcggc tatttctgct     840
cgcgtgcacc cgactctatt acctgtgtcc cacccactgg cgtcggtaaa caagtccttt     900
aatgcaatct tgttgaagc agaagcagct ggtcgcctga tgttctacgg aaacggtgca     960
ggtggcgcgc caaccgcgtc tgctgtgctt ggcgacgtcg ttggtgccgc acgaaacaag    1020
gtgcacggtg ccgtgctcc aggtgagtcc acctacgcta acctgccgat cgctgatttc    1080
ggtgagacca ccactcgtta ccacctcgac atggatgtgg aagatcgcgt gagcgttttg    1140
gctgaattgg ctagcctgtt ctctgagcaa ggaatctccc tgcgtacaat ccgacaggaa    1200
gagcgcgatg atgatgcacg tctgatcgtg gtcacccact ctgcgctgga atctgatctt    1260
tcccgcaccg ttgaactgct gaaggctaag cctgttgtta aggcaatcaa cagtgtgatc    1320
cgcctcgaaa gggactaa                                                  1338
```

<210> SEQ ID NO 10
<211> LENGTH: 445
<212> TYPE: PRT
<213> ORGANISM: Artificial Sequence
<220> FEATURE:
<223> OTHER INFORMATION: Hom (KFCC10881-1)

<400> SEQUENCE: 10

```
Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110
```

Ser Val Val Thr Ala Asn Lys Ala Leu Val Ala Ala His Ser Ala Glu
            115                 120                 125

Leu Ala Asp Ala Ala Glu Ala Ala Asn Val Asp Leu Tyr Phe Glu Ala
        130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Gly Lys Phe Thr Asn Lys
            260                 265                 270

Glu Gly Lys Ser Ala Ile Ser Ala Arg Val His Pro Ile Leu Leu Pro
        275                 280                 285

Val Ser His Pro Leu Ala Ser Val Asn Lys Ser Phe Asn Ala Ile Phe
        290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Arg Ala Pro Gly Glu Ser Thr Tyr
            340                 345                 350

Ala Asn Leu Pro Ile Ala Asp Phe Gly Glu Thr Thr Thr Arg Tyr His
        355                 360                 365

Leu Asp Met Asp Val Glu Asp Arg Val Gly Val Leu Ala Glu Leu Ala
        370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
        435                 440                 445

<210> SEQ ID NO 11
<211> LENGTH: 445
<212> TYPE: PRT
<213> ORGANISM: Artificial Sequence
<220> FEATURE:
<223> OTHER INFORMATION: Hom (KFCC10881-14)

<400> SEQUENCE: 11

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

-continued

```
Val Met Arg Leu Met Thr Glu Tyr Gly Asp Glu Leu Ala His Arg Ile
         35                  40                  45

Gly Gly Pro Leu Glu Val Arg Gly Ile Ala Val Ser Asp Ile Ser Lys
 50                  55                  60

Pro Arg Glu Gly Val Ala Pro Glu Leu Leu Thr Glu Asp Ala Phe Ala
 65                  70                  75                  80

Leu Ile Glu Arg Glu Asp Val Asp Ile Val Glu Val Ile Gly Gly
                 85                  90                  95

Ile Glu Tyr Pro Arg Glu Val Val Leu Ala Ala Leu Lys Ala Gly Lys
                100                 105                 110

Ser Val Val Thr Ala Asn Lys Ala Leu Val Ala Ala His Ser Ala Glu
                115                 120                 125

Leu Ala Asp Ala Ala Glu Ala Ala Asn Val Asp Leu Tyr Phe Glu Ala
            130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
            195                 200                 205

Ala Asp Val Glu Gly His Asp Ala Ala Ser Lys Ala Ala Ile Leu Ala
            210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
            275                 280                 285

Val Ser His Pro Leu Ala Ser Val Asn Lys Ser Phe Asn Ala Ile Phe
290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
            340                 345                 350

Ala Asn Leu Pro Ile Ala Asp Phe Gly Glu Thr Thr Thr Arg Tyr His
            355                 360                 365

Leu Asp Met Asp Val Glu Asp Arg Val Gly Val Leu Ala Glu Leu Ala
    370                 375                 380

Ser Leu Phe Ser Glu Gln Gly Ile Ser Leu Arg Thr Ile Gln Gln Glu
385                 390                 395                 400

Glu Arg Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
            435                 440                 445
```

<210> SEQ ID NO 12
<211> LENGTH: 445
<212> TYPE: PRT
<213> ORGANISM: Artificial Sequence
<220> FEATURE:
<223> OTHER INFORMATION: Hom (KFCC10881-19)

<400> SEQUENCE: 12

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
    290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
            340                 345                 350

Ala Asn Leu Pro Ile Ala Asp Phe Gly Glu Thr Thr Thr Arg Tyr His
        355                 360                 365

```
Leu Asp Met Asp Val Glu Asp Arg Val Trp Val Leu Ala Glu Leu Ala
        370                 375                 380

Ser Leu Phe Ser Glu Gln Gly Ile Ser Leu Arg Thr Ile Arg Gln Glu
385                 390                 395                 400

Glu Arg Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
                420                 425                 430

Val Lys Ala Ile Asn Ser Val Ile Arg Leu Glu Arg Asp
                435                 440                 445

<210> SEQ ID NO 13
<211> LENGTH: 445
<212> TYPE: PRT
<213> ORGANISM: Artificial Sequence
<220> FEATURE:
<223> OTHER INFORMATION: Hom (KFCC10881-22)

<400> SEQUENCE: 13

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
                20                  25                  30

Val Met Arg Leu Met Thr Glu Tyr Gly Asp Glu Leu Ala His Arg Ile
            35                  40                  45

Gly Gly Pro Leu Glu Val Arg Gly Ile Ala Val Ser Asp Ile Ser Lys
        50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285
```

Val Ser His Pro Leu Ala Ser Val Asn Lys Ser Phe Asn Ala Ile Phe
290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Arg Ala Pro Gly Glu Ser Thr Tyr
                340                 345                 350

Ala Asn Leu Pro Ile Ala Asp Phe Gly Glu Thr Thr Arg Tyr His
                355                 360                 365

Leu Asp Met Asp Val Glu Asp Arg Val Ser Val Leu Ala Glu Leu Ala
370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
                420                 425                 430

Val Lys Ala Ile Asn Ser Val Ile Arg Leu Glu Arg Asp
        435                 440                 445

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
tcgagctcgg taccctgcg acagcatgga actc                               34

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
ctctagagga tccccttagt ccctttcgag gcgg                              34

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
caccggcgct gactatgc                                                18

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
aatcgggtgc acgcgagc                                                18

```
<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
ttggattgta cgcaggga                                                 18

<210> SEQ ID NO 19
<211> LENGTH: 18
<212> TYPE: DNA
<213> ORGANISM: Artificial Sequence
<220> FEATURE:
<223> OTHER INFORMATION: primer

<400> SEQUENCE: 19
ccacacgcga tcttccac                                                 18

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
gctcacgcga tcttccac                                                 18

<210> SEQ ID NO 21
<211> LENGTH: 18
<212> TYPE: DNA
<213> ORGANISM: Artificial Sequence
<220> FEATURE:
<223> OTHER INFORMATION: primer

<400> SEQUENCE: 21
ttagtccctt tcgaggcg                                                 18

<210> SEQ ID NO 22
<211> LENGTH: 421
<212> TYPE: PRT
<213> ORGANISM: Artificial Sequence
<220> FEATURE:
<223> OTHER INFORMATION: lysC(L377K)

<400> SEQUENCE: 22
```

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly 115                 120                 125
Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Lys Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 23
<211> LENGTH: 34
<212> TYPE: DNA
<213> ORGANISM: Artificial Sequence
<220> FEATURE:
<223> OTHER INFORMATION: primer

<400> SEQUENCE: 23
tcgagctcgg tacccgctgc gcagtgttga atac        34

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
tggaaatctt ttcgatgttc acgttgacat     30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
atgtcaacgt gaacatcgaa aagatttcca     30

<210> SEQ ID NO 26
<211> LENGTH: 34
<212> TYPE: DNA
<213> ORGANISM: Artificial Sequence
<220> FEATURE:
<223> OTHER INFORMATION: primer

<400> SEQUENCE: 26
ctctagagga tccccgttca cctcagagac gatt     34

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
acggatccca gactccaaag caaaagcg     28

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
acaccacggc agaaccaggt gcaaaggaca     30

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
ctggttctgc cgtggtgtgc atcatctctg     30

<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
acggatccaa ccaaacttgc tcacactc     28

<210> SEQ ID NO 31
<211> LENGTH: 1161

```
<212> TYPE: DNA
<213> ORGANISM: Artificial Sequence
<220> FEATURE:
<223> OTHER INFORMATION: metB gene

<400> SEQUENCE: 31
ttgtcttttg acccaaacac ccagggtttc tccactgcat cgattcacgc tgggtatgag      60
ccagacgact actacggttc gattaacacc ccaatctatg cctccaccac cttcgcgcag     120
aacgctccaa acgaactgcg caaaggctac gagtacaccc gtgtgggcaa ccccaccatc     180
gtggcattag agcagaccgt cgcagcactc gaaggcgcaa agtatggccg cgcattctcc     240
tccggcatgg ctgcaaccga catcctgttc cgcatcatcc tcaagccggg cgatcacatc     300
gtcctcggca acgatgctta cggcggaacc taccgcctga tcgacaccgt attcaccgca     360
tggggcgtcg aataccaccgt tgttgatacc tccgtcgtgg aagaggtcaa ggcagcgatc     420
aaggacaaca ccaagctgat ctgggtggaa accccaacca acccagcact ggcatcacc      480 gacatcgaag cagtagcaaa gctcaccgaa ggcaccaacg ccaagctggt tgttgacaac     540
accttcgcat ccccataccct gcagcagcca ctaaaactcg gcgcacacgc agtcctgcac     600
tccaccacca agtacatcgg aggacactcc gacgttgttg gcggccttgt ggttaccaac     660
gaccaggaaa tggacgaaga actgctgttc atgcagggcg gcatcggacc gatcccatca     720
gttttcgatg catacctgac cgcccgtggc ctcaagaccc ttgcagtgcg catggatcgc     780
cactgcgaca acgcagaaaa gatcgcggaa ttcctggact cccgcccaga ggtctccacc     840
gtgctctacc caggtctgaa gaaccaccca ggccacgaag tcgcagcgaa gcagatgaag     900
cgcttcggcg gcatgatctc cgtccgtttc gcaggcggcg aagaagcagc taagaagttc     960
tgtacctcca ccaaactgat ctgtctggcc gagtccctcg gtggcgtgga atccctcctg    1020
gagcacccag caaccatgac ccaccagtca gctgccggct ctcagctcga ggttccccgc    1080
gacctcgtgc gcatctccat tggtattgaa gacattgaag acctgctcgc agatgtcgag    1140
caggccctca ataacctta g                                               1161

<210> SEQ ID NO 32
<211> LENGTH: 24
<212> TYPE: DNA
<213> ORGANISM: Artificial Sequence
<220> FEATURE:
<223> OTHER INFORMATION: primer

<400> SEQUENCE: 32
tctagacgcc cgcatactgg cttc                                              24

<210> SEQ ID NO 33
<211> LENGTH: 37
<212> TYPE: DNA
<213> ORGANISM: Artificial Sequence
<220> FEATURE:
<223> OTHER INFORMATION: primer

<400> SEQUENCE: 33
cccatccact aaacttaaac agatgtgatc gcccggc                                37

<210> SEQ ID NO 34
<211> LENGTH: 38
<212> TYPE: DNA
<213> ORGANISM: Artificial Sequence
<220> FEATURE:
<223> OTHER INFORMATION: primer
```

<400> SEQUENCE: 34
tgtttaagtt tagtggatgg ggaagaacca cccaggcc                             38

<210> SEQ ID NO 35
<211> LENGTH: 23
<212> TYPE: DNA
<213> ORGANISM: Artificial Sequence
<220> FEATURE:
<223> OTHER INFORMATION: primer

<400> SEQUENCE: 35
gtcgaccaat cgtccagagg gcg                                             23

<210> SEQ ID NO 36
<211> LENGTH: 1314
<212> TYPE: DNA
<213> ORGANISM: Artificial Sequence
<220> FEATURE:
<223> OTHER INFORMATION: metY gene

<400> SEQUENCE: 36
atgccaaagt acgacaattc caatgctgac cagtggggct ttgaaacccg ctccattcac     60
gcaggccagt cagtagacgc acagaccagc gcacgaaacc ttccgatcta ccaatccacc    120
gctttcgtgt tcgactccgc tgagcacgcc aagcagcgtt tcgcacttga ggatctaggc    180
cctgtttact cccgcctcac caacccaacc gttgaggctt ggaaaaccg catcgcttcc     240 ctcgaaggtg gcgtccacgc tgtagcgttc tcctccggac aggccgcaac caccaacgcc    300
attttgaacc tggcaggagc gggcgaccac atcgtcacct ccccacgcct ctacggtggc    360
accgagactc tattccttat cactcttaac cgcctgggta tcgatgtttc cttcgtggaa    420
aaccccgacg accctgagtc ctggcaggca gccgttcagc aaacaccaa agcattcttc     480 ggcgagactt tcgccaaccc acaggcagac gtcctggata ttcctgcggt ggctgaagtt    540
gcgcaccgca acagcgttcc actgatcatc gacaacacca tcgctaccgc agcgctcgtg    600
cgcccgctcg agctcggcgc agacgttgtc gtcgcttccc tcaccaagtt ctacaccggc    660
aacggctccg gactgggcgg cgtgcttatc gacggcggaa agttcgattg gactgtcgaa    720
aaggatggaa agccagtatt ccccctacttc gtcactccag atgctgctta ccacggattg    780
aagtacgcag accttggtgc accagccttc ggcctcaagg ttcgcgttgg ccttctacgc    840
gacaccggct ccaccctctc cgcattcaac gcatgggctg cagtccaggg catcgacacc    900
ctttccctgc gcctggagcg ccacaacgaa aacgccatca aggttgcaga attcctcaac    960
aaccacgaga aggtggaaaa ggttaacttc gcaggcctga aggattcccc ttggtacgca    1020
accaaggaaa agcttggcct gaagtacacc ggctccgttc tcaccttcga gatcaagggc    1080
ggcaaggatg aggcttgggc atttatcgac gccctgaagc tacactccaa ccttgcaaac    1140
atcggcgatg ttcgctccct cgttgttcac ccagcaacca ccacccattc acagtccgac    1200
gaagctggcc tggcacgcgc gggcgttacc cagtccaccg tccgcctgtc cgttggcatc    1260
gagaccattg atgatatcat cgctgacctc gaaggcggct tgctgcaat ctag          1314

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
tctagaccat cctgcaccat ttag                                               24

<210> SEQ ID NO 38
<211> LENGTH: 37
<212> TYPE: DNA
<213> ORGANISM: Artificial Sequence
<220> FEATURE:
<223> OTHER INFORMATION: primer

<400> SEQUENCE: 38
cccatccact aaacttaaac acgctcctgc caggttc                                 37

<210> SEQ ID NO 39
<211> LENGTH: 39
<212> TYPE: DNA
<213> ORGANISM: Artificial Sequence
<220> FEATURE:
<223> OTHER INFORMATION: primer

<400> SEQUENCE: 39
tgtttaagtt tagtggatgg gcttggtacg caaccaagg                               39

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
gtcgacgatt gctccggctt cgg                                                23

<210> SEQ ID NO 41
<211> LENGTH: 2213
<212> TYPE: DNA
<213> ORGANISM: Artificial Sequence
<220> FEATURE:
<223> OTHER INFORMATION: mcbR gene

<400> SEQUENCE: 41
aatctggatt tccgccaggt tttggcacgc ccgtctggtt taggcaatga gataccgaac        60
acacgtgcca aaagttcggc ttttttcgccg atcttgtcac gcctgcctgg tttgtcttgt     120
aaagagtgat ttcatggccg agactcctaa aagtttgacc tcacaggatt gcttctaagg      180
gcctctccaa tctccactga ggtacttaat ccttccgggg aattcgggcg cttaaatcga      240
gaaattaggc catcaccttt taataacaat acaatgaata attggaatag gtcgacacct      300
ttggagcgga gccggttaaa attggcagca ttcaccgaaa gaaaaggaga accacatgct      360
tgccctaggt tggattacat ggatcattat tggtggtcta gctggttgga ttgcctccaa      420
gattaaaggc actgatgctc agcaaggaat tttgctgaac atagtcgtcg gtattatcgg      480
tggtttgtta ggcggctggc tgcttggaat cttcggagtg gatgttgccg gtggcggctt      540
gatcttcagc ttcatcacat gtctgattgg tgctgtcatt ttgctgacga tcgtgcagtt      600
cttcactcgg aagaagtaat ctgctttaaa tccgtagggc ctgttgatat ttcgatatca      660
acaggccttt tggtcatttt ggggtggaaa aagcgctaga cttgcctgtg gattaaaact      720
atacgaaccg gtttgtctat attggtgtta gacagttcgt cgtatcttga aacagaccaa      780
cccgaaagga cgtggccgaa cgtggctgct agcgcttcag gcaagagtaa aacaagtgcc      840
ggggcaaacc gtcgtcgcaa tcgaccaagc ccccgacagc gtctcctcga tagcgcaacc      900

```
aaccttttca ccacagaagg tattcgcgtc atcggtattg atcgtatcct ccgtgaagct    960
gacgtggcga aggcgagcct ctattcccct ttcggatcga aggacgcctt ggttattgca   1020
tacctggaga acctcgatca gctgtggcgt gaagcgtggc gtgagcgcac cgtcggtatg   1080
aaggatccgg aagataaaat catcgcgttc tttgatcagt gcattgagga agaaccagaa   1140
aaagatttcc gcggctcgca ctttcagaat gcggctagtg agtaccctcg ccccgaaact   1200
gatagcgaaa agggcattgt tgcagcagtg ttagagcacc gcgagtggtg tcataagact   1260
ctgactgatt tgctcactga aagaacggc tacccaggca ccacccaggc gaatcagctg   1320
ttggtgttcc ttgatggtgg acttgctgga tctcgattgg tccacaacat cagtcctctt   1380
gagacggctc gcgatttggc tcggcagttg ttgtcggctc cacctgcgga ctactcaatt   1440
tagtttcttc attttccgaa ggggtatctt cgttggggga ggcgtcgata agccccttct   1500
ttttagcttt aacctcagcg cgacgctgct ttaagcgctg catggcggcg cggttcattt   1560
cacgttgcgt ttcgcgcctc ttgttcgcga tttctttgcg ggcctgtttt gcttcgttga   1620
tttcggcagt acgggttttg gtgagttcca cgtttgttgc gtgaagcgtt gaggcgttcc   1680
atggggtgag aatcatcagg gcgcggtttt tgcgtcgtgt ccacaggaag atgcgctttt   1740 cttttgttt tgcgcggtag atgtcgcgct gctctaggtg gtgcactttg aaatcgtcgg   1800
taagtgggta tttgcgttcc aaaatgacca tcatgatgat tgtttggagg agcgtccaca   1860
ggttgttgct gacccaatag agtgcgattg ctgtggggaa tggtcctgtg aggccaaggg   1920
acagtgggaa gatcggcgcg aggatcgaca tcacgatcat gaacttcagc atgccgttag   1980
agaatccgga tgcgtaatcg ttggtttgga agctgcggta catggacatc gccatgttga   2040
ttgcggtgag gattgcggct gtgatgaaca gtggcaaaac gaaactaaga acttccgcct   2100
gcgtggtgct caaatatttt agctgctcag tgggcatcga aacataagcg ggcagaggca   2160
cattgctcac gcgaccagcg aggaaagatt ccacttcctc aggagttagg aag          2213
```

```
<210> SEQ ID NO 42
<211> LENGTH: 28
<212> TYPE: DNA
<213> ORGANISM: Artificial Sequence
<220> FEATURE:
<223> OTHER INFORMATION: primer

<400> SEQUENCE: 42
ggcccgggcc tgcctggttt gtcttgta                                         28

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
cggaaaatga agaaagttcg gccacgtcct ttcgg                                 35

<210> SEQ ID NO 44
<211> LENGTH: 35
<212> TYPE: DNA
<213> ORGANISM: Artificial Sequence
<220> FEATURE:
<223> OTHER INFORMATION: primer

<400> SEQUENCE: 44
aggacgtggc cgaactttct tcattttccg aaggg                                 35
```

```
<210> SEQ ID NO 45
<211> LENGTH: 28
<212> TYPE: DNA
<213> ORGANISM: Artificial Sequence
<220> FEATURE:
<223> OTHER INFORMATION: primer

<400> SEQUENCE: 45
atcccggggt ttcgatgccc actgagca                                         28

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
aatctggatt tccgccaggt                                                  20

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
cttcctaact cctgaggaag                                                  20

<210> SEQ ID NO 48
<211> LENGTH: 1338
<212> TYPE: DNA
<213> ORGANISM: Artificial Sequence
<220> FEATURE:
<223> OTHER INFORMATION: wild-type hom gene

<400> SEQUENCE: 48
atgacctcag catctgcccc aagctttaac cccggcaagg gtcccggctc agcagtcgga      60
attgcccttt taggattcgg aacagtcggc actgaggtga tgcgtctgat gaccgagtac     120
ggtgatgaac ttgcgcaccg cattggtggc ccactggagg ttcgtggcat tgctgtttct     180
gatatctcaa agccacgtga aggcgttgca cctgagctgc tcactgagga cgcttttgca     240
ctcatcgagc gcgaggatgt tgacatcgtc gttgaggtta cggcggcat tgagtaccca     300
cgtgaggtag ttctcgcagc tctgaaggcc ggcaagtctg ttgttaccgc caataaggct     360
cttgttgcag ctcactctgc tgagcttgct gatgcagcgg aagccgcaaa cgttgacctg     420
tacttcgagg ctgctgttgc aggcgcaatt ccagtggttg ccccactgcg tcgctccctg     480
gctggcgatc agatccagtc tgtgatgggc atcgttaacg gcaccaccaa cttcatcttg     540
gacgccatgg attccaccgg cgctgactat gcagattctt tggctgaggc aactcgtttg     600
ggttacgccg aagctgatcc aactgcagac gtcgaaggcc atgacgccgc atccaaggct     660
gcaattttgg catccatcgc tttccacacc cgtgttaccg cggatgatgt gtactgcgaa     720
ggtatcagca acatcagcgc tgccgacatt gaggcagcac agcaggcagg ccacaccatc     780
aagttgttgg ccatctgtga agttcacc aacaaggaag gaaagtcggc tatttctgct     840
cgcgtgcacc cgactctatt acctgtgtcc cacccactgg cgtcggtaaa caagtccttt     900
aatgcaatct ttgttgaagc agaagcagct ggtcgcctga tgttctacgg aaacggtgca     960
```

```
ggtggcgcgc caaccgcgtc tgctgtgctt ggcgacgtcg ttggtgccgc acgaaacaag      1020
gtgcacggtg ccgtgctcc aggtgagtcc acctacgcta acctgccgat cgctgatttc       1080
ggtgagacca ccactcgtta ccacctcgac atggatgtgg aagatcgcgt ggggttttg       1140 gctgaattgg ctagcctgtt ctctgagcaa ggaatctccc tgcgtacaat ccgacaggaa      1200
gagcgcgatg atgatgcacg tctgatcgtg gtcacccact ctgcgctgga atctgatctt     1260
tcccgcaccg ttgaactgct gaaggctaag cctgttgtta aggcaatcaa cagtgtgatc     1320
cgcctcgaaa gggactaa                                                    1338
```

<210> SEQ ID NO 49
<211> LENGTH: 445
<212> TYPE: PRT
<213> ORGANISM: Artificial Sequence
<220> FEATURE:
<223> OTHER INFORMATION: ATCC14067 hom (NCgl1136)

<400> SEQUENCE: 49

```
Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
                20                  25                  30

Val Met Arg Leu Met Thr Glu Tyr Gly Asp Glu Leu Ala His Arg Ile
            35                  40                  45

Gly Gly Pro Leu Glu Val Arg Gly Ile Ala Val Ser Asp Ile Ser Lys
        50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
```

```
            290                 295                 300
Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Arg Ala Pro Gly Glu Ser Thr Tyr
            340                 345                 350

Ala Asn Leu Pro Ile Ala Asp Phe Gly Glu Thr Thr Thr Arg Tyr His
            355                 360                 365

Leu Asp Met Asp Val Glu Asp Arg Val Gly Val Leu Ala Glu Leu Ala
        370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
                420                 425                 430

Val Lys Ala Ile Asn Ser Val Ile Arg Leu Glu Arg Asp
        435                 440                 445

<210> SEQ ID NO 50
<211> LENGTH: 445
<212> TYPE: PRT
<213> ORGANISM: Artificial Sequence
<220> FEATURE:
<223> OTHER INFORMATION: ATCC13869 hom

<400> SEQUENCE: 50

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
```

```
            210                 215                 220
Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
                260                 265                 270

Glu Gly Lys Ser Ala Ile Ser Ala Arg Val His Pro Thr Leu Leu Pro
            275                 280                 285

Val Ser His Pro Leu Ala Ser Val Asn Lys Ser Phe Asn Ala Ile Phe
            290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
                340                 345                 350

Ala Asn Leu Pro Ile Ala Asp Phe Gly Glu Thr Thr Thr Arg Tyr His
                355                 360                 365

Leu Asp Met Asp Val Glu Asp Arg Val Gly Val Leu Ala Glu Leu Ala
            370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
                420                 425                 430

Val Lys Ala Ile Asn Ser Val Ile Arg Leu Glu Arg Asp
                435                 440                 445
```